(12) United States Patent
Abraham

(10) Patent No.: US 8,235,903 B2
(45) Date of Patent: Aug. 7, 2012

(54) REMOTELY CONTROLLED IMPLANTABLE TRANSDUCER AND ASSOCIATED DISPLAYS AND CONTROLS

(75) Inventor: Theodore P. Abraham, Baltimore, MD (US)

(73) Assignee: InnoScion, LLC, Baltimore, MD (US)

( * ) Notice: Subject to any disclaimer, the term of this patent is extended or adjusted under 35 U.S.C. 154(b) by 131 days.

(21) Appl. No.: 12/700,066

(22) Filed: Feb. 4, 2010

(65) Prior Publication Data

US 2010/0174189 A1 Jul. 8, 2010

Related U.S. Application Data

(63) Continuation-in-part of application No. 12/285,779, filed on Oct. 14, 2008, and a continuation-in-part of application No. 12/182,247, filed on Jul. 30, 2008, and a continuation-in-part of application No. 11/871,219, filed on Oct. 12, 2007.

(60) Provisional application No. 61/149,729, filed on Feb. 4, 2009.

(51) Int. Cl.
*A61N 7/00* (2006.01)
*A61B 8/00* (2006.01)

(52) U.S. Cl. .......................... 600/439; 600/459

(58) Field of Classification Search .................. 600/302, 600/407, 437, 439, 443–448, 459; 601/2–4; 128/903
See application file for complete search history.

(56) References Cited

U.S. PATENT DOCUMENTS

| | | | |
|---|---|---|---|
| 4,109,644 A | 8/1978 | Kojima | |
| 5,027,659 A * | 7/1991 | Bele et al. | 73/626 |
| 5,100,424 A * | 3/1992 | Jang et al. | 606/159 |
| 5,161,204 A | 11/1992 | Hutcheson et al. | |
| 5,247,938 A * | 9/1993 | Silverstein et al. | 600/459 |
| 5,255,684 A * | 10/1993 | Rello | 600/463 |
| 5,273,632 A | 12/1993 | Stockham et al. | |
| 5,374,527 A | 12/1994 | Grossman | |
| 5,409,005 A * | 4/1995 | Bissonnette et al. | 600/437 |

(Continued)

FOREIGN PATENT DOCUMENTS

WO 03056494 7/2003

(Continued)

OTHER PUBLICATIONS

Chen, Jingkuang et al., "Implantable Ultrasound Emitter Array for Medical Applications," IEEE, MEMS 2006, Istanbul, Turkey, Jan. 22-26, 2006, pp. 422-425.

(Continued)

*Primary Examiner* — Francis Jaworski
(74) *Attorney, Agent, or Firm* — Cameron LLP

(57) ABSTRACT

An implantable, remotely controlled medical device that incorporates an imaging/therapy ultrasound system may be minimally invasive and equipped with an anchoring portion for securing the device within a human body. Transducers for imaging/therapy may be manipulated remotely using motors and/or selectively actuated to obtain different fields of view and stereoscopic imaging. The implantable medical device can be in the shape of a disc, double disc, sphere or pellet, for example, and may be implanted during open surgery using a manipulatable tool or using a minimally invasive image-guided sheath or catheter. The imaging system comprises one or more ultrasound transducers and can be used to provide therapy to or obtain ultrasound images of a target and surrounding volumes or focal points. The device may be controlled and report data by wired or wireless means and, if wireless, permanently worn inside the body as the patient follows their normal daily routine.

13 Claims, 11 Drawing Sheets

U.S. PATENT DOCUMENTS

| | | | |
|---|---|---|---|
| 5,454,373 A | | 10/1995 | Koger et al. |
| 5,465,724 A | | 11/1995 | Sliwa, Jr. et al. |
| 5,471,988 A | * | 12/1995 | Fujio et al. ............... 600/439 |
| 5,541,067 A | | 7/1996 | Perlin |
| 5,580,728 A | | 12/1996 | Perlin |
| 5,630,416 A | * | 5/1997 | Uchikura et al. ............ 600/444 |
| 5,704,361 A | | 1/1998 | Seward et al. |
| 5,715,825 A | * | 2/1998 | Crowley ..................... 600/462 |
| 5,759,369 A | | 6/1998 | Menchen et al. |
| 5,844,140 A | * | 12/1998 | Seale ............................ 73/633 |
| 5,876,933 A | | 3/1999 | Perlin |
| 6,054,268 A | | 4/2000 | Perlin |
| 6,066,096 A | | 5/2000 | Smith et al. |
| 6,131,459 A | * | 10/2000 | Seale et al. ...................... 73/633 |
| 6,454,716 B1 | * | 9/2002 | Zumeris ....................... 600/453 |
| 6,741,983 B1 | | 5/2004 | Birdwell et al. |
| 6,750,011 B1 | | 6/2004 | Perlin |
| 6,807,490 B1 | | 10/2004 | Perlin |
| 6,936,003 B2 | * | 8/2005 | Iddan ............................ 600/114 |
| 7,118,531 B2 | | 10/2006 | Krill |
| 7,270,634 B2 | * | 9/2007 | Scampini et al. .............. 600/447 |
| 7,319,781 B2 | * | 1/2008 | Chen et al. ..................... 382/128 |
| 7,637,865 B2 | | 12/2009 | Iddan et al. |
| 7,914,452 B2 | * | 3/2011 | Hartley et al. ................ 600/439 |
| 8,005,536 B2 | * | 8/2011 | Imran ............................ 600/547 |
| 2002/0086289 A1 | | 7/2002 | Straus |
| 2002/0152035 A1 | | 10/2002 | Perlin |
| 2003/0143554 A1 | | 7/2003 | Berres et al. |
| 2003/0195415 A1 | * | 10/2003 | Iddan ............................ 600/424 |
| 2007/0066894 A1 | | 3/2007 | Bartol et al. |
| 2008/0208057 A1 | | 8/2008 | Hoctor et al. |

FOREIGN PATENT DOCUMENTS

| WO | WO2007014292 A2 | 2/2007 |
|---|---|---|

OTHER PUBLICATIONS

Ellozy, Sharif H. et al., "First Experience in Human Beings with a Permanently Implantable Intrasac Pressure Transducer for Monitoring Endovascular Repair of Abdominal Aortic Aneurysms," Journal of Vascular Surgery, Sep. 2004, pp. 405-412.

Perlin, Mark W. et al., "Linear Mixture Analysis: A Mathematical Approach to Resolving DNA Samples," Journal Forensic Science, 2001, vol. 46, No. 6, pp. 1372-1378.

Wang, Tsewei, "Commentary," Journal Forensic Science, Sep. 2002, published Aug. 21, 2002, vol. 47, No. 5, Paper ID JFS2002092_475.

Perlin, Mark W., "Authors Response," Journal Forensic Science, Sep. 2002, published Aug. 21, 2002, vol. 47, No. 5, Paper ID JFS2002123_475.

Schwartz, Lisa S. et al., "Fluorescent Multiplex Linkage Analysis and Carrier Detection for Duchenne/Becker Muscular Distrophy," Am. J. Human Genetics 51:721-729, 1992.

McConkey, E. H., "Human Genetics: The Molecular Revolution," Jones and Bartlett Publishers, 1993, pp. 92-112.

Clayton, T. M. et al., "Analysis and Interpretation of Mixed Forensic Stains Using DNA STR Profiling," Forensic Science International, vol. 91, pp. 55-70, 1998.

Gill P. et al., "Interpreting Simple STR Mixtures Using Allele Peak Areas," 1998, Forensic Science International, vol. 91, pp. 41-53.

Evett, Ian W. et al., "Taking Account of Peak Areas When Interpeting Mixed DNA Profiles," 1998, Journal of Forensic Sciences, vol. 43. No. 1, pp. 62-69.

Perlin, Mark W. et al., "Toward Fully Automated Genotyping: Genotyping Microsatellite Markers by Deconvolution," 1995, American Journal of Human Genetics, vol. 57, pp. 1199-1210.

Wang, Tsewei et al., "Mixture STR/DNA Deconvolution Using Allele Peak Area Data and the Least Square Technique," 12th International Symposium on Human Identification, Biloxi, MS, Oct. 9-12, 2001.

* cited by examiner

| TRANSDUCER TRANSCEIVER ID | X | Y | ANGLE OF ROTATION | ANGLE OF TWIST OF ARRAY | ON/OFF | FOCUS CONTROL | DRR |

{ MOTOR CONTROL }

FIG. 4A

| WORKSTATION TRANSCEIVER ID | IMAGE DATA | X | Y | ANGLE OF ROTATION |

{ ACTUAL DATA }

FIG. 4B

PELLET VERSION (SOLID) FOR CATHETER DELIVERY

REMOTELY CONTROLLED IMPLANTABLE TRANSDUCER AND ASSOCIATED DISPLAYS AND CONTROLS

CROSS-REFERENCE

This application is a continuation-in-part of U.S. patent application Ser. No. 12/285,779, filed Oct. 14, 2008; U.S. patent application Ser. No. 12/182,247, filed Jul. 30, 2008; and U.S. patent application Ser. No. 11/871,219, filed Oct. 12, 2007, and claims the benefit of priority to U.S. Provisional Patent Application Ser. No. 61/149,729, filed Feb. 4, 2009, all four of which applications are by the same inventor and are incorporated by reference herein in their entirety.

TECHNICAL FIELD

Illustrated and disclosed aspects relate to an implantable ultrasound transducer, transducer array or plurality of transducers for selectively imaging a body from within the body, remotely and selectively controlling the images obtained from the transducer, transducer array or plurality of transducers and displaying the selected images from the transducers or from a delivery and installation catheter or sheath, for example, outside the body via a wireless display mounted on the delivery and installation catheter or sheath.

BACKGROUND

Ultrasound operates by creating an image from sound in three steps—producing a sound wave, receiving echoes, and interpreting those echoes to create an image. Invasive ultrasonic apparatus is known for imaging areas of the human body and has found many diagnostic and therapeutic uses such as guiding therapeutic instruments through a catheter to a field of view within a human body. As will be described below, a wireless implantable transducer is known for suturing to the heart organ. A transmitter transmits power and control information to the implantable transducer. An output of heart function is provided on an oscilloscope. Moreover, image-guided catheters are generally known for intravascular or endoscopic or other guide wire or penetrating approach to reach and then travel through body lumen. An image-guided may be used to deliver a tool or another item to a target area within a patient, for example, to deliver a vascular stent to a target site in a vascular system where there is impeded blood flow or to deliver a scalpel to remove suspicious matter during endoscopic procedures.

For example, U.S. Pat. No. 5,704,361 to Seward et al. discloses a volumetric image ultrasound transducer underfluid catheter system. FIGS. 2-9 and 11-12 and their attendant description, for example, suggest specific methods of intervention for imaging purposes in the vicinity of a human heart. To reach such an area of interest within a human body, an ultrasound imaging and hemodynamic catheter may be advanced via the superior vena cava of the heart to a tricuspid valve annulus. A distal end of a cylindrical body includes a guide wire access port and a guide wire provides a means of assuring that the catheter reaches a target human heart for imaging. A surgical tool may be fed through the catheter to the area imaged.

U.S. Pat. No. 4,109,644 to Kojima of Aug. 29, 1978, may represent an early development of a miniature implantable ultrasonic echosonometer. An ultrasonic transducer may be attached, for example, by stitches to an organ, for example, the heart of a living body that is to be measured. The ultrasonic transmitter/receiver circuit communicates via antenna to an external "readout" device such as an oscilloscope. No battery is required for the echosonometer. Induced power may be received from a power receiver loop for powering the ultrasonic transmitter/receiver circuit.

U.S. Pat. No. 5,454,373 issued Oct. 3, 1995, to Koger et al. describes a rotatable drive shaft of an ultrasound imaging device having a tubular body and a nose member which includes the ultrasound imaging device and connected to the rotatable drive shaft for rotation to obtain different internal views, for example, of a blood vessel.

U.S. Pat. No. 5,465,724, issued Nov. 14, 1995 to Sliwa, Jr. et al. discloses a compact rotationally steerable ultrasound transducer having a circular track or a carrier band operable to rotate a multi-element transducer, for example, for transesophegal echocardiography.

U.S. Pat. No. 7,118,531, issued Oct. 10, 2006, to Krill describes an ingestible medical payload carrying capsule with wireless, e.g. ultrasonic, communication to transducers placed on a patient. The capsule may deliver medication or contain imaging apparatus such as an optical camera and/or a transducer with a pulse driver for internal acoustic pulse illumination and external high resolution sonogram imaging and detection.

U.S. Published Patent Application, US 2007/0066894 to Bartol et al., published Mar. 22, 2007, describes a remote wireless control device for an ultrasound machine and method. The remote wireless control device includes a subset of controls present on larger apparatus including a sonogram display. A smaller mobile unit communicates with the larger unit and may be more easily used bed-side than the larger apparatus.

U.S. Published Patent Application, US 2008/0208057 to Hoctor et al., published Aug. 28, 2008, discloses a method and apparatus for non-invasive ultrasonic fetal rate monitoring whereby a cMUT (capacitive micromachined ultrasonic transducer) patch adheres to a mother's abdomen and cMUT sub-elements may be grouped together using a reconfigurable electronic switching network, for example, to actuate annular arrays of sub-elements per FIGS. 5, 7 and 8.

U.S. Pat. No. 7,637,865 to Iddan et al. of Dec. 29, 2009, describes an in vivo imaging device that is, for example, substantially spherical in shape (although it may be ellipsoidal) and may be swallowed. It may be weighted intentionally so that it is oriented by the pull of gravity as the device travels through a gastro-intestinal tract. In one embodiment, the field of view of a CMOS or CCD image sensor camera may be 80-90 degrees or even 80-140 degrees with a focus distance of between 0 to 40 mm (or slightly less than two inches). Power may be provided by silver oxide, lithium or other electro-chemical cells having a high energy density or induced from an external source.

WO 2007/014292 A2, published Feb. 1, 2007, discloses an ultrasound apparatus where an angularly rotating transducer head enables a cylinder roller to move back and forth by a rotating motor at an angle of −45 degrees to +45 degrees on the tissue surface. An embodiment of a volumetric scanning probe 1500 is depicted in FIGS. 15A-15B in top view and a side cut-away view. A transducer head 1508 is mounted at the periphery of a cylindrical roller 1504 driven by a motor/actuator in a manner that angularly sweeps the cylindrical roller 1504 back and forth between about −45 degrees and +45 relative to a normal to the tissue surface.

Further, ultrasound has trouble penetrating bone and, thus, for example, ultrasound imaging of the brain and heart area are limited, for example, by the skull bone and the ribs, respectively. Ultrasound also does not perform well when there is gas present (as in the gastrointestinal tract and lungs).

Still further, a highly skilled and experienced ultrasound operator is necessary to obtain quality images. These drawbacks do not, however, limit the usefulness of ultrasound as a medical diagnostic and treatment tool.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

Illustrative aspects described herein include a minimally invasive, medical device in the form of an implantable ultrasonic transducer that can provide ultrasound imaging in a selective manner by preferably wireless transmission/reception to an external transceiver and display (although wired or cabled transmission/reception is also useful in some embodiments). Selective viewing is achieved by selective or switched transducer actuation in a multi-transducer system and/or by operating miniature motors for moving one or more transducers, for example, to rotate, twist, or move a selected transducer in a linear direction or even, in some embodiments two, orthogonal, linear directions.

Monitoring of organ structure and function, for example, the structure and function of the brain, heart, lungs, kidneys and liver, among other organs, on a very frequent or, if required, continuous basis may be required in certain medical situations such as after chest or abdominal surgery or when the function of the organ is impaired by disease. While ultrasound may be a common method of monitoring organ structure and function, there exist physical and logistic limitations to a frequent or continuous use of ultrasound examination, for example, due to the large size of the ultrasound apparatus required and the requirement for a skilled technician to interpret the imaging results.

U.S. Published Patent Application US 2009/0036780, published Feb. 5, 2009, of the same inventor, describes a wired or wireless, remotely controlled ultrasonic transducer and imaging apparatus which may be secured to the skin surface of a patient and its output ultrasound directed internally to a living body during use. An associated transducer may be used for therapeutic or diagnostic imaging purposes. The disclosed apparatus thus provides some solution to the large size disadvantage of known ultrasound imaging apparatus. The device, when fixed to the skin surface of a patient, can monitor, for example, heart or other organ operation, for example, according to known and predictable organ operation such as heart rate or pulse and blood pressure or other predictable organ operation. For example, in pre-operative situations, such as fetal monitoring, the disclosed remotely manipulatable transducer element or linear transducer array can replace large, bulky bedside apparatus and communicate via wired or wireless means with a remote work station where a skilled technician may interpret imaging results. Moreover, the device may be worn by the patient and provide immediate warnings to the patient of, for example, an irregular heart beat and the like. On the other hand, in many post-operative patients or trauma patients, there may be a chest or abdominal wound or dressing and, while the disclosed device in one embodiment may be installed within the dressing, the transducer device may not be applied directly to the skin or the sterile dressing may have to be removed to obtain improved imaging. In either case, imaging may not be possible from an ideal skin surface location and if applied at another location, the transducer range may be such that the image quality may not be optimal resulting in a lack of imaging and other derivable information and the need for additional, for example, bed-side apparatus and processes to supplement the collection of structure and function data of an impacted organ.

The Krill pill solution of providing an ingestible imaging device provides transient images. Once the pill passes a target area, the opportunity to provide imaging is lost. The pill, by its nature, is moving through, for example, the digestive tract. Some efforts have been made to slow down its passage or to weight it so that it may be more stationary. On the other hand, a pill imaging device may turn and twist as it passes through a patient and make imaging difficult. Besides such a device not being stationary, the device may not be useable in, for example, the skull to monitor brain function, monitor structure and function of organs or monitor muscle or joint movement among other locations within the human body on a more permanent basis. Similarly, the remotely controlled skin surface-mounted device may not be permanently fixed to the skin surface absent painful stitching and possible infection and may be inadvertently become inoperable while worn by the patient, for example, if adhesive material is used to secure the device to the patient's skin and the adhesive material comes loose.

On the other hand, an internally embedded and secured imaging transducer according to embodiments and aspects described herein may permit wired or wireless remote imaging on demand, whenever desired, patient alarms and frequent or periodic, if not continuous, monitoring without fear of the transducer becoming loose or no longer operable. Embodiments of the present implantable device may selectively monitor a recent surgical site, the structure and function of organs, for example, the brain, and muscular and joint function and provide therapies, for example, for blood clotting or tumors, from within a body without fear of being dislodged.

An implanted device of one or more embodiments may be customized to include other forms of data collection including, but not limited to fiber optic or CCD or CMOS imaging, pressure sensing, infrared imaging, thermal sensing, pressure sensing, optical coherence tomography (OCT) imaging and other possible data collection so long as the monitoring apparatus may be miniaturized so as to not impede normal body function or cause the patient pain. As described in prior applications of the same inventor, an ultrasound transducer device may be equipped with auxiliary capabilities, for example, to deliver therapy such as thermal energy from low frequency ultrasound emission which can generate heat, for example, or otherwise dissolve blood clots or shrink tumors.

The frequencies present in a sound wave output of a transducer of an implantable device can range between 0.01 (approximately 10 kHz) and 250 MHz. The upper range of ultrasound may exceed 1 GHz within the next twenty years. Consequently, 250 MHz should not be construed to be limiting as an upper bound. The very high frequency range including 250 MHz provides very high resolution, also known as bio-microscopy applications. Since an implanted device of one or more embodiments may be implanted in close proximity with tissue of a target site (for example, depth of field of view is not as important has high resolution), higher frequencies are especially useful, for example, for characterization of tissue pathology. The lower frequencies, for example, between 10 kHz and 5 MHz may be used for therapeutic purposes and the higher frequencies, for example, between 1 MHz and 250 MHz for imaging data collection including, for example, bio-microscopy applications. Therapeutic uses include treatment of tumors and dissolution of blood clots, among other applications. For imaging, the higher the frequency, the greater the image resolution but the depth of imaging decreases with increasing frequency.

A field of view of an implanted ultrasonic imaging device according to the several embodiments may be maximized if the device is in the form of a disc, a pellet or a sphere. In the disc embodiment, the disc may be double-sided and more resemble a pill with a rounded top and bottom and cylindrical sides. For example, transducers may be provided on both sides of a motor-containing and/or electronics-containing cylindrical housing for moving and/or selecting the transducers to achieve a 360° spherical field of view.

In one embodiment, a disc-shaped implantable transducer is provided with a rotatable and twistable transducer located along the diameter of a transducer disc housing top to be implanted, for example, using an imaging catheter and/or sheath as described in U.S. patent application Ser. No. 12/285,779 filed Oct. 14, 2008 of the same inventor and recently published as US 2009/0105597 on Apr. 23, 2009. By top and bottom, as used herein, the top will face a primary organ to which it may be secured and imaged while the bottom may face outward from the body organ to be imaged. According to the several embodiments, a linear or phased array transducer of such a disc-shaped implantable device with variable and selectable ultrasound frequency output may be implanted and secured at a target location by one or more of suturing, a screw and tines. U.S. patent application Ser. No. 11/871,219 filed Oct. 12, 2007, of the same inventor provides details of an anchoring portion of an ultrasound image guided catheter/sheath having first and second deployable balloons for positioning the image guided catheter so as to be fixed to an internal body wall such as a pericardial wall for minimally invasive medical procedures. The first and second deployable balloon anchoring may be utilized with or in place of a screw and/or tines in one or more of the implantable devices of the several embodiments to secure the device, for example, to an exterior lining of the pericardium for imaging the heart or other internal wall sandwiched between the balloons. At the target location, the implantable device may, for example, provide images, detect and output body function parameters or provide therapy, among other functions.

A catheter and/or sheath, for example, as disclosed in the '779 application may be used to reach a target site for the implantable device, penetrate an organ lining with an introducer needle and deliver and install the implantable transducer. If a patient is already opened during surgery, the implantable transducer of the several embodiments may be sutured in an optimum location during the surgery to monitor the surgical site (and selected surrounding views) or provide necessary therapies. The sutures may be absorbable sutures so that they may disappear within a matter of a week or two and the implantable device may be pulled out by an attached wire or cable (which may be used for external communication). In one embodiment, the device is placed in a saturable jacket—the jacket and sutures being bioabsorbable. Consequently, the jacket may be absorbed along with the sutures and the implantable device removed by a cable.

An introducer needle of such a catheter and/or sheath, under forward-facing ultrasonic transducer guidance and, optionally, further guidance provided by the remotely controlled surface-mounted wireless transducer, may be used to reach and to puncture the target site if required. The introducer needle may then be removed from the catheter/sheath and an implantable device may then move along a guide wire through the catheter, sheath to the target site or be delivered by a manipulatable shaft as will be further described herein. A top of the implantable device of the several embodiments may be sutured or screwed or actuated via tines via the delivery catheter or sheath or manipulatable shaft tool to adhere and be secured to the target site or in surrounding tissue. Also, as will be discussed herein, first and second deployable balloons may be inflated to sandwich an internal body wall with the implantable device.

The ultrasound features of an implanted device can serve to guide and facilitate further surgical procedures performed using the implanted device for imaging guidance. For example, a medical professional such as a surgeon can receive direct vision of a targeted area in real time from an implanted device of one of the several embodiments. Moreover, use of an implanted device according to one or more aspects herein can significantly reduce post-surgical events such as clotting after a particular surgical procedure is performed.

An implanted device may provide imaging on demand of volumes within reach of the field of view of associated transducers. For example, the implantable ultrasound transducer device may be implanted in the chest cavity and so selectively obtain image data of the structure and function of the lungs, heart and organs of the abdominal cavities without visible limitation by bone. Thus, for example, many procedures can be performed through minimally invasive surgical techniques or non-invasive procedures where more invasive surgical procedures have been previously required. The implanted device of the several embodiments may deliver warnings to a patient wearing the implanted device, for example, of irregular rhythms, pressures or other extraordinary detectable events.

The disc embodiment may be alternatively constructed of first and second transducer arrays (one at a top and one at a bottom so as to form a pill shape) and associated rotation and twist motors for viewing, for example, if placed in the vicinity of the heart and so attached to the pericardium, in directions toward the heart and away from the heart in practically a 360° field of view.

A spherical embodiment (or disc or pellet) embodiment may have no motors for moving transducers. In such an embodiment, a plurality of transducers, transducer arrays or sub-elements as defined herein are placed evenly about the sphere (disc or pellet), for example, in non-obtrusive apertures. Transducer sub-elements are connected to a processor and selectively or switchably actuated individually or in selected combinations. Via wireless (or wired) means, for example, a latitude and longitude coordinate or equivalent, depending on the degree of motor movement use, a rotational coordinate, is transmitted to the spherical (or disc or pellet) implantable transducer. An electronic circuit thereof switchably enables a sector of sub-elements or a plurality of spaced sub-elements for therapy or imaging. These then may be actuated at a frequency for therapy or for imaging or for both therapy and imaging. If imaging, the selected transducers or sub-elements report imaging data of the selected ultrasonic view from the enabled sector, combination of transducers via wireless means to an external receiver for display. As defined herein, a sub-element of a transducer, transducer array or plurality of transducers or transducer arrays is the smallest individual unit that is selectively actuable and may cover the smallest field of outward view that is individually actuable by the electronic circuit. A sector may be defined as a combination of contiguous transducer sub-elements capable of imaging/providing therapy to an internal body volume simultaneously.

A pellet-shaped embodiment may be equipped with either two motors, for example, for linear movement along the pellet and rotational movement about the cross-section of the pellet so that a given transducer, transducer array or sub-element may be moved along its length for example by a screw turned by a rotation motor, linearly, and rotated about the circumference of the pellet through 360° via a rotation motor. In a related embodiment, a linear array of transducers, the length of the pellet, is rotated by a single motor through a 360° circumference of the pellet according to a selected angle of rotation. In a further related pellet embodiment, a plurality of transducers are placed along its length and spaced about its circumference, for example, in apertures to cover the surface of the pellet. These may comprise sub-elements and may be selectively actuated in a similar manner as the spherical embodiment briefly discussed above.

The pellet (disc or sphere) embodiment may be solid and delivered by a manipulatable tool or have a central lumen and guide wire for delivery to a target site. An advantage of a manipulatable tool is that the tool with the pellet to be installed at its distal end may turn a securing screw, actuate extendable securing tines, inflate a pair of sandwiching balloons and release the pellet at the target site (or similarly, by reversing the process, remove the pellet).

Implantable devices in the form of a disc, a pellet and/or a sphere may be secured in place by suturing, by a screw (turned by a tool moving within or without the delivery lumen of a catheter/sheath), by extendable tines or by sandwiching balloons, that may be actuated/deactivated/inflated by the same catheter or sheath or a combination of one or more screws and tines and sutures and dual balloons. As suggested above, the same catheter or sheath device utilized to deliver the implantable device to a target area inside the body may also be utilized to perform suturing, turn the screw, actuate the tines and inflate a pair of sandwiching balloons. In a reverse manner, the implantable device may be removed by an imaging catheter or sheath or other manipulatable tool.

Catheter and sheath delivery devices as discussed herein for delivering and installing the implantable devices of the various embodiments can be effectively utilized for intracardiac treatments via pericardial (heart) or other organ access, without entry through blood vessels. Such devices can also be especially useful in diagnosing and treating loculated or compartmentalized effusions in the heart (pericardial), abdomen (ascites), chest, or abcesses in any organ or body cavity. The real-time imaging that can be provided by implantable devices of the disc, pellet and spherical embodiments can allow safe and accurate imaging and be installed in multiple body compartments and ensure safe and long-lasting usage through a combination of battery power and induction battery charging as is known in the art in combination with catheter/sheath imaging/therapy and/or remotely controlled surface mounted imaging/therapy.

In some embodiments according to aspects herein, a display may be mounted on an imaging catheter or sheath. For example, the catheter may be one as shown, for example in FIG. 8B of the '779 application. In accordance with embodiments disclosed herein, one or more small displays are mounted at the proximal end of the imaging catheter/sheath.

A delivery sheath may have a cross-section similar to FIG. 16D of the '779 application where the forceps channel 1650 is, instead, used for an introducer needle and also for manipulatable tool delivery of an implantable device of a disc, pellet or sphere embodiment and also used for its installation according to U.S. patent application Ser. No. 12/285,779 filed Oct. 14, 2008 of the same inventor. FIGS. 17A and 17B of the '779 application further suggests use of a channel such as channel 1650 for use in creating a suction attachment to an organ wall (such as the pericardium 1700 or an internal lining thereof) for, for example, suturing, screwing, tine actuation or balloon inflation for attachment of a disc, pellet, or spherical implantable transducer device to secure the device to an internal wall, lining or other tissue.

According to aspects herein, the casing of an implantable disc, pellet or sphere transducer imaging device may be formed from one or more of a variety of materials such as silicone, Teflon, polyurethane, PVC, and/or elastomeric hydrogel. Preferably the casing or housing is transparent to ultrasound and is of a biocompatible (non-bioreactive) material so that the transducers may be either embedded in the housing surface (for example, a switchably selectable multi-transducer embodiment) or mounted just below their surface (for example, a single transducer, array or sub-element embodiment) being motor driven to a position for outward facing imaging or combination of motor movement and selective actuation.

In an exemplary procedure of accessing the pericardium and delivering and installing an implantable device, an image-guided catheter or sheath device can be advanced, for example, to a patient's pericardium while using one or more ultrasound front-facing transducers to guide insertion and advancement of the elongate body of the catheter/sheath to the target organ or other site within a body, for example, the heart. Such an exemplary procedure can include puncturing the pericardial lining with a needle under front-facing ultrasound guidance as the catheter/sheath device is advanced (for example, as a starter hole for a screw mounting or a double sandwiching balloon inflation or to gain access within the outer pericardial lining to reach the inner lining) while imaging the pericardial lining using the one or more front-facing ultrasound transducers. The needle is then removed and a manipulatable tool with the implantable transducer temporarily attached to its distal end and/or a guide wire for advancing the implantable disc, pellet or sphere to the target site may be utilized with front-facing ultrasonic imaging of the catheter/sheath to deliver the disc, pellet or sphere implantable device housing to the target site. A guide wire may be provided, for example, through a lumen of the pellet (disc or sphere) and, in turn, the elongate body of the catheter or sheath may be used to place the pellet (disc or sphere) at the target site. In accordance with one aspect, the pellet (disc or sphere) is equipped with a screw (which may serve a second purpose as an RF antenna) and the screw turned so as to secure the pellet (disc or sphere) in the pericardium or pericardial cavity interior or exterior lining. A double balloon means of securing an implantable device of one or more embodiments in place of a screw and/or tines will be discussed further herein.

These and other aspects will be discussed with reference to the drawings, a brief description of which follows.

BRIEF DESCRIPTION OF THE DRAWINGS

The above-described aspects and embodiments of devices and procedures and other features and advantages can be appreciated and understood by reference to the following detailed description when considered in connection with the accompanying drawings wherein:

FIG. 5, sphere or FIGS. 7-9, pellet, which may communicate wirelessly (or by wire) with a work station outside a living body during use of the implantable device. The schematic block diagram shows a transducer control unit and memory and a wireless transceiver in addition to a radio (wireless) transceiver connected to the transducer control unit. Also shown are a battery power supply (which may further be inductively charged, not shown), one motor for rotating a linear transducer element array, two motors for optionally moving the array in perpendicular X and Y directions and one motor for twisting the array as well as analog to digital and data compression circuitry for converting collected ultrasound image data to digital form for transmission via a radio transceiver.

FIG. 4A provides an exemplary signal content format for providing motor control of an implantable transducer, transducer array or plurality of transducers of FIG. 1 (disc), 5 (sphere) or 7-9 (pellet) in a direction from a work station to the implantable transducer including a unique transducer transceiver identifier if wireless or telecommunications transmission is utilized. The format also provides for known and herein introduced control such as on/off, focus, ultrasound frequency of operation, power level, depth (related to frequency), magnification or zoom, mode, time and date and the like. Moreover, image data may be transmitted as will be explained with reference to FIG. 4B and subsequently received at the transceiver for verification with transmitted data stored in local memory 207 (FIG. 2), 607 (FIG. 6).

FIG. 4B provides an exemplary signal content format for providing a reply signal from an implantable transducer or transducer array of FIG. 1, 5 or 7-9 in a direction from an implantable transducer to a destination external to the body in which a device is implanted including a unique work station or display identifier if wireless or telecommunications transmission is utilized toward the work station/display or an associated server. The depicted format provides for feedback of actual location data of the position of the implanted transducer or transducer array, time and date of image data (not shown), as well as image data collected for that location and time and date.

DETAILED DESCRIPTION

Figure 1A:
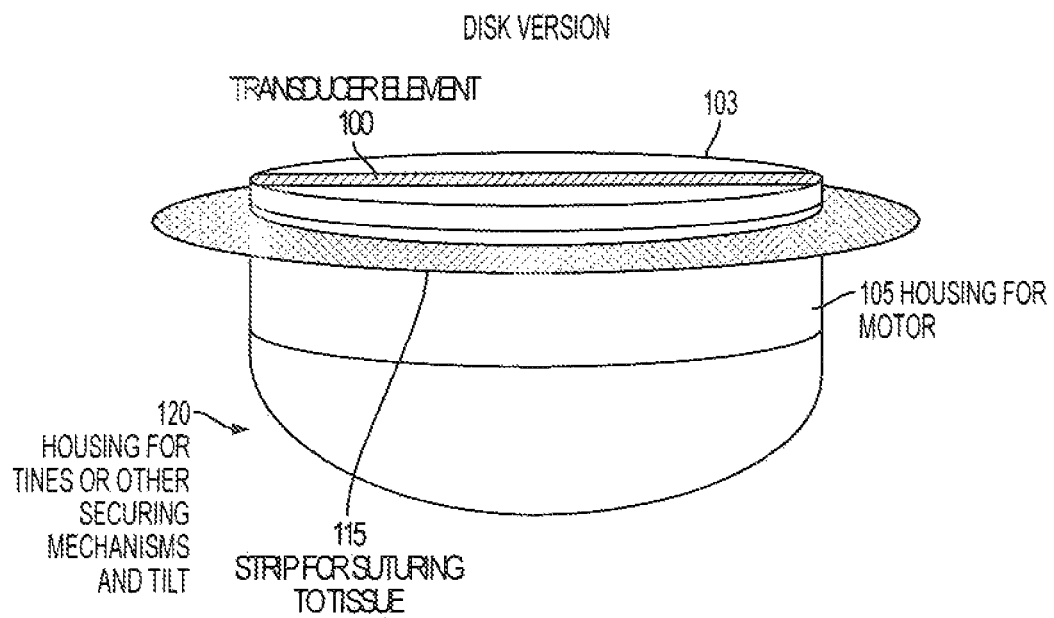
FIG. 1A shows a side, surface view of one embodiment of a minimally invasive implantable transducer in the shape of a disc.

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made or combined into alternative embodiments than those depicted, without departing from the scope of the present disclosure.

Minimally invasive procedures can provide physicians with access to internal organs and structures via a small number of incisions in the patients' body, preferably one small incision. Using this approach, the treatment area can be directly accessed by creating such a small incision and inserting an imaging catheter or sheath, for example, one shown in U.S. application Ser. No. 12/285,779 filed Oct. 14, 2008, of the same inventor through the incision which serves as an entry port through which an implantable ultrasound transducer device embodiment according to one of FIGS. 1, 5 and 7-9 and installation tools therefor are passed. Alternatively, access to a target site for an implantable device will be provided during surgery. Moreover, access can sometimes be obtained using a natural bodily opening such as the throat or trachea, nasal opening, oral, ear or rectum or other body opening and the implantable device secured therein. In such procedures, an imaging catheter or sheath can be inserted into the body opening and an implantable transducer is delivered, either through the catheter/sheath or directly through the body or surgical opening, to a target site.

Minimally invasive procedures may generally be preferable over open procedures because they can require only small incisions, can reduce trauma to the body, can lessen recovery time, and can reduce costs. The medical catheter/sheath used in performing such procedures may generally be similar to those used in open surgical procedures except that they may include an elongate body such as a tubular extension between the distal end of the instrument entering the surgical field (i.e., the operable end of the tool, instrument or device) and the proximal portion gripped by the surgeon.

While minimally invasive procedures may provide numerous advantages over open procedures, they generally do not provide a physician with a direct view of the targeted sites. Further, many parts of the anatomy are rather complex and/or small and, thus, require particular precision and delicate handling. Therefore, it may be necessary to provide precise imaging techniques for use during minimally invasive procedures, for example, surface imaging and catheter/sheath imaging as taught by U.S. application Ser. No. 12/285,779, filed Oct. 14, 2008 of the same inventor.

In certain minimally invasive procedures, a visualization tool or guide, such as an endoscope, laparoscope, laryngoscope, etc., also can be inserted to the vicinity of the target site so that, as the surgeon manipulates instruments at the target site, the surgeon is able to view the procedure of implanting an implantable transducer on a video monitor.

For example, endoscopes are used during an endoscopic procedure, which is a procedure performed on the digestive system. The endoscope is a flexible tube that incorporates a camera and light and allows visualization inside the body. The endoscope can be inserted through the mouth or anus to access any portion of the digestive system. While endoscopy does not require the creation of incisions and allows for visualization of a site prior to and during surgery, endoscopes are relatively expensive and are obscured by blood and other biological materials. Further, endoscopes are capable only of viewing the surfaces of structures such as nasal passages or the lining of the colon, and cannot provide visualization of what is inside of or beyond structures unless they incorporate ultrasound or other imaging capability that may see through a body wall.

Laparoscopes are used during laparoscopic procedures, which are performed on a patient's abdomen or pelvis, including the fallopian tubes, ovaries, uterus, small bowel, large bowel, appendix, liver, and gallbladder. During a laparoscopic procedure, a telescopic instrument called a laparoscope is inserted into the abdomen through a small incision at the belly button. A camera attached to the laparoscope allows surgeons to view inside the abdomen and perform the procedures without having to make a large incision. Usually, four more small incisions are made in the abdomen to accommodate surgical instruments, typically through cannulas or sleeves, during the procedure. As with endoscopes, laparoscopes are capable only of viewing structures and cannot provide visualization of what is inside of or beyond structures unless they are further equipped with ultrasound.

Another common imaging technique that can be used to visualize a patient's internal structures is tomography. Tomography provides imaging by sections or sectioning. Computed tomography (CT) can use digital geometry processing to generate a three-dimensional image of the internals of an object from a large series of two dimensional X-ray images taken around a single axis of rotation. However, CT is regarded as a moderate to high radiation diagnostic technique. Further, because CT scans rely on intravenously administered contrast agents in order to provide high image quality, there is a risk associated with the contrast agents. Certain patients may experience severe and even life-threatening allergic reactions to the contrast agents. Further, the contrast agents can induce kidney damage. With patients who have preexisting renal insufficiency, preexisting diabetes, or reduced intravascular volume, this risk is increased. Further, CT cannot be used during a procedure and, thus, is not sufficient for use in procedures on anatomical structures that are subject to motion such as, for example, the heart. CT may be used to assist, however, imaging data output of an implantable ultrasound transducer.

Magnetic resonance imaging (MRI), formerly referred to as magnetic resonance tomography (MRT) or nuclear magnetic resonance (NMR), is a method used to visualize the inside of living organisms as well as to detect the composition of geological structures. Like CT, MRI is not performed during a procedure and is insufficient for use in procedures on anatomical structures that are subject to motion. Further, MRI devices are very expensive and require significant upkeep costs. While CT scanner uses ionizing radiation, X-rays, to provide images, MRI uses radio frequency signals. Thus, CT is good for dense tissue (e.g. bone), while MRI is best suited for soft (non-calcified) tissue. MRI also cannot be performed on patients with pacemakers because arrhythmias or even death can result. Ferromagnetic foreign bodies or metallic implants (e.g. surgical prosthesis) also present potential risks for MRI. Interaction between the magnetic and radio frequency fields with these bodies can cause the bodies to move and result in trauma, and radio frequency induction heating of the bodies can also cause thermal injury. Further, some individuals with even mild claustrophobia may be unable to tolerate an MRI scan. It is recommended that any implantable device of the several embodiments not include iron so that MRI may assist ultrasonic imaging therefrom. For example, any wireless antenna may be of a precious metal such as gold.

The devices and methods relating to an embodiment of an implantable imaging transducer primarily illustrated in FIGS. 1, 5 and 7-9 and described herein can be used in a wide variety of minimally invasive surgical procedures and with additional imaging as described above in various surgical and data-collecting procedures. While capsules are known, for example, from Krill, it is a feature of the embodiments described herein that they be unobtrusively secured for an extended duration within a human body cavity or secured to an organ or other tissue, for example, proximate to a joint or muscle area to be monitored for structure and function. In addition, one skilled in the art will appreciate that the aspects and embodiments of FIGS. 1, 5 and 7-9, although advantageously suited for such procedures on humans, can be used in veterinary procedures and in open medical techniques as well. Further, while the devices of the present invention are described with particular reference to implantable transducers in the shape of a disc, pellet, sphere or pill, this shall not be construed as limiting the devices to these embodiments, however, as it is contemplated and thus within the scope of the illustrated devices to adapt the devices described herein so as to be in the form of any type of minimally invasive implantable device in any shape and for providing selected viewing or therapy in as many directions and as large a field of view at as many depths and resolutions as are capable by the implanted transducers, for example, according to frequency and power of operation.

Further, while certain devices, systems and methods are described herein with particular reference to pericardial access devices, systems, and methods, this shall not be construed as limiting, as it is contemplated to adapt the implantable ultrasound selective imaging devices, systems and methods described herein so as to be used to assist in any of a number of procedures, including, but not limited to, various cardiovascular procedures, general micro-surgery, drug and device delivery, vascular procedures, urology, thoracic procedures, otorhinolaryngology (ear, nose and throat), orthopedic procedures, neurosurgery, gynecologic procedures, gastroenterologic and general procedures, colon and rectal procedures, pericardiocentesis, thoracentesis, ascites tap, ventricular lead placements, and electrical and electro-mechanical mapping of the heart. As such, it is contemplated that the specific design parameters, other characteristics set forth hereinafter, and methods in relation thereto can be modified as required so as to provide the appropriate dimensions and geometries as required to perform such other techniques. For example, the length and diameter of a disc, pellet, spherical or pill implantable device as herein described may be adapted to suit the particular conditions for a given procedure and can be further modified to suit conditions for a different procedure and a different target organ or area within a body. Thus, the disclosure to follow should be construed as illustrative rather than in a limiting sense.

In general, the illustrated embodiments and aspects provide an implantable ultrasound device that couples an imaging/therapy system and a transceiver system that are remotely controlled to provide selected ultrasound imaging/therapy in a given direction, field of view, resolution by means of motors and/or selective actuation of transducers, arrays or sub-elements. A delivery system for an implantable device embodiment can include, for example, a catheter or sheath for direct entry through the skin to a target site for delivery of the implantable ultrasonic imaging device to the target site. In certain embodiments, the implantable device incorporates one or more selectable and/or variable frequency ultrasound transducers operating at one or more selected frequencies within the frequency range of 0.01-250 MHz and at varying power levels, for example, higher power levels for tumor treatment. The imaging system of the implanted device may guide and facilitate various procedures and diagnostic applications, for example, bio-microscopy, thereby significantly assisting in the access of and performance of procedures and diagnosis on various organs, structures and body cavities within the body, particularly during minimally invasive procedures, but applicable to surgical procedures as well. Frequencies above 1 MHz may be used to provide imaging, including bio-microscopy, where the higher the frequency, the greater the resolution possible but the lesser the depth reachable in the human body from an actuated transducer or sub-element to a target site. As described above, frequencies in a lower frequency range of, for example, 10 kHz to 5 MHz may provide therapeutic heat, clot dissolution and cancerous tumor therapies.

Ultrasound provides particular benefits because it is biologically safe and uses non-radiating energy to provide detailed anatomic and, depending on the application, functional images. The images and/or parameters or therapeutic treatments generated by the present implantable devices provide a user with direct vision or therapy within the body in real time on demand or continuously. Further, ultrasound provides a user with visualization of other structures as well as within and beyond target structures. The described implantable devices and methods are compatible with practically any surgical and diagnostic device and will aid bedside emergency procedures. For example, it may be appropriate to fix an implantable ultrasound imaging device proximate to a cardiac pacemaker or to couple a device to a cardiac pacemaker or heart assist (pump) device in a patient for imaging the heart as it is paced or assisted. Another assist example may be an insulin pump or other implantable medication delivery device.

Figure 2:
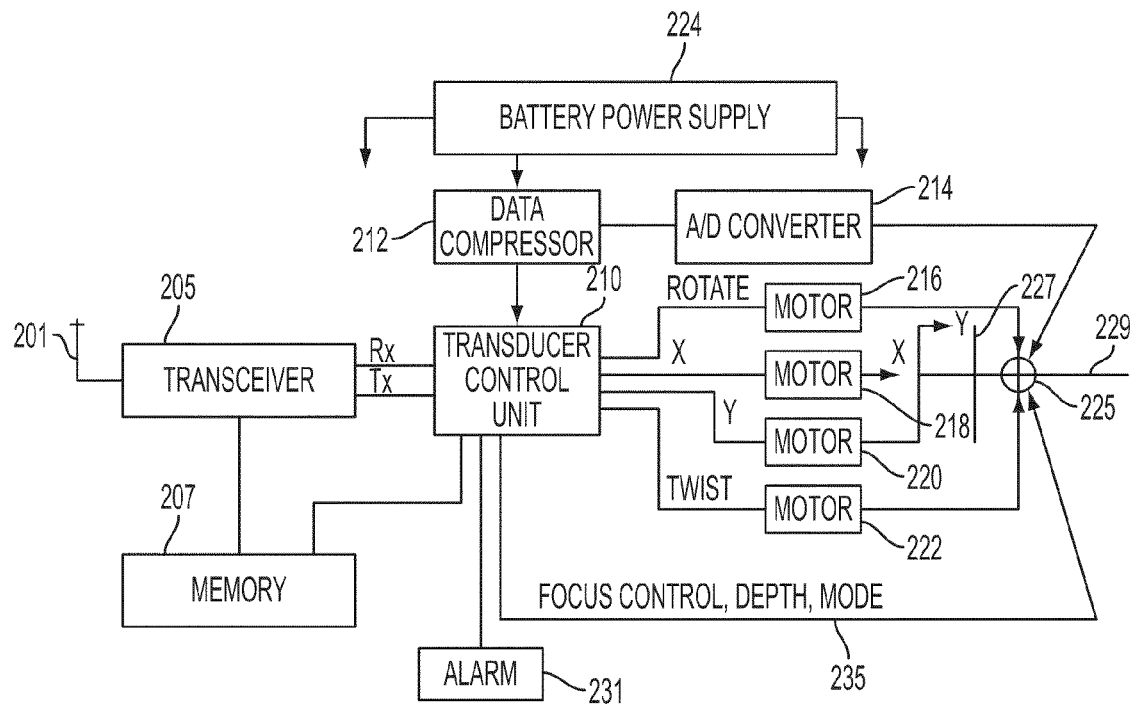
FIG. 2 provides a schematic block diagram for implantable device embodiments and aspects as shown in FIG. 1, disc.
Figure 3:
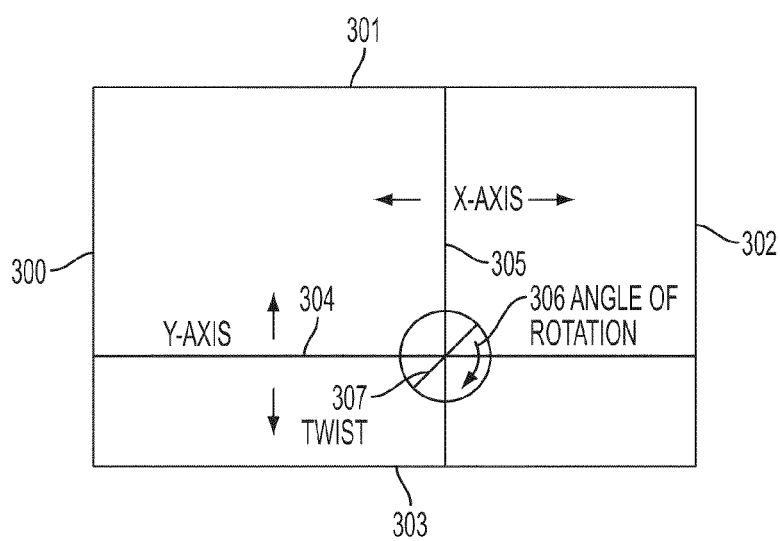
FIG. 3 provides an overview of a mechanical arrangement to be contained within a housing of embodiments of an implantable transducer assembly unit as necessary comprising rods and motors for manipulating a transducer or linear transducer array in two perpendicular directions, for example, along an x axis and a y axis, to rotate a transducer through a selected angle of rotation, for example, to permit multiple image planes and to twist a transducer to a selected angle of twist to redirect a sound wave emitted by a transducer or linear array of transducer elements whereby it is envisioned that a footprint on an organ surface is rectangular or square and may relate to the disc, sphere and pellet embodiments and circuits of FIGS. 1, 2, 5 and 7-9 if the arrangement is contained therein.
Figure 5A:
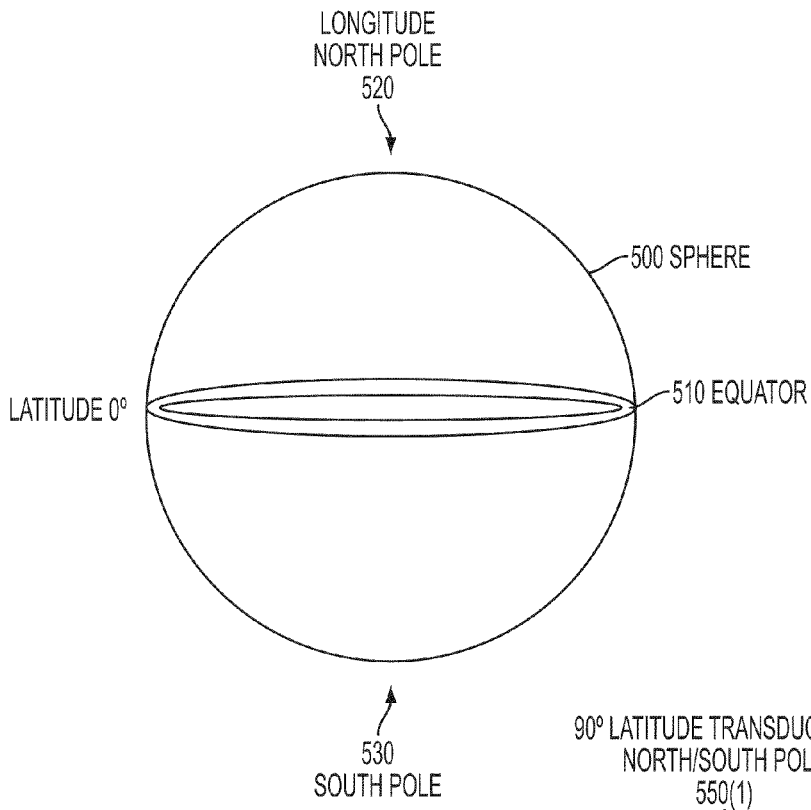
FIG. 5A shows a side view of a spherical implantable transducer device in accordance with aspects herein where 0° latitude represents a ring analogous to the equator of the earth and 90° latitude represents the north or south pole while 0° longitude is represented by a vertical line in FIG. 5C.

Referring now to the various figures of the drawings wherein like reference characters refer to like parts, FIGS. 1, 5 and 7-9 depict various views of a minimally invasive implantable device 100 of one or more embodiments: disc, pellet, sphere or other shape, such as a double disc or pill shape. FIGS. 2, 3 and 6 relate to either movement of a sub-element or selection/actuation of a sub-element. FIG. 4 relates to exemplary data parameters for a given transmit or receive wireless or wired channel. Implantable devices according to these various embodiments may be of a motor type and/or of an electronically switchably selectable type for selectively viewing or providing therapy to a volume or desired field of view surrounding the secured, implanted device.

FIG. 1 comprises a side view (FIG. 1A) and a top view (FIG. 1B) of a first plurality of disc shaped implantable embodiments and aspects of a multi-plane transducer unit comprising, for example, a rotatable linear array 100 of transducer elements including a housing 103, which may have a curved top surface. The rotatable linear (or phased) array 100 may be aligned along a diameter of the top of housing 103 (and in a pill shape, a similar diameter of a bottom housing, not shown). By top surface, as used herein, top refers to a side pointing toward an internal organ to be imaged and/or treated by the transducer array 100. The housing 103 comprising transducer element 100 may be mounted by securing material, for example, suturing material 115 to an internal organ body or internal tissue of, for example, a patient (not shown). Suturing material 115 may be bioabsorbable and so the device may be easily removed once the material and sutures are absorbed or suturing material 115 and associated sutures may be permanently placed. In the case of repeat surgery or an open wound, the sutures may be cut and the implantable device manually retrieved. In the disc embodiment of FIGS. 1A and 1B, the top or other surface may be provided with a screw as an alternative to suturing material 115 and as may be seen in FIG. 9 for the pellet embodiment. For further securing the device or in the alternative, a screw (not shown) may be provided; a housing 120 may be provided for extendable tines and/or double balloons; (see FIG. 9 for an example of tines, a screw and alternate positions for double balloons in the tines' extended, balloons inflated position). A manipulatable shaft 910 may be used to deliver and install the disc by turning the screw, extend the tines or inflate the balloons (distal balloon first) to sandwich a body wall or lining.

The transducer array 100 or sub-element thereof may be remotely controllably rotated or twisted by wired or wireless means and be otherwise remotely controlled by wireless signals transmitted toward the housings 103, 105 from a remote work station (not shown) or by a control and retrieval lead (not shown) to the disc remaining, for example, after surgery. An operator need not be proximate the patient's body to manipulate or control the movement or selection of a transducer array 100 or selected sub-element thereof.

Similar reference numbers will be used throughout the detailed description to refer to similar elements wherein the first number of the reference number may denote the figure in which an element first appears in detail. For example, rotation motor 216 and twist motor 222 for transducer 100 (FIG. 1) are first shown in detail in FIG. 2. Transducer 100 may comprise a single transducer element for ultrasonic transmission and reception of reflected sound waves, a preferably linear array 100 of transducer elements or a plurality of selectable sub-elements. These may have selectable frequency and power level of operation for imaging/therapy or different resolution, depth and actuation capability mounted, for example, in a linear manner from a top perspective as a diameter of a circle. In one embodiment, not shown, a single transducer may be mounted at the center of the circle comprising housing 103 and moved along the diameter of the circle linearly as well as twisted and rotated.

Figure 1B:
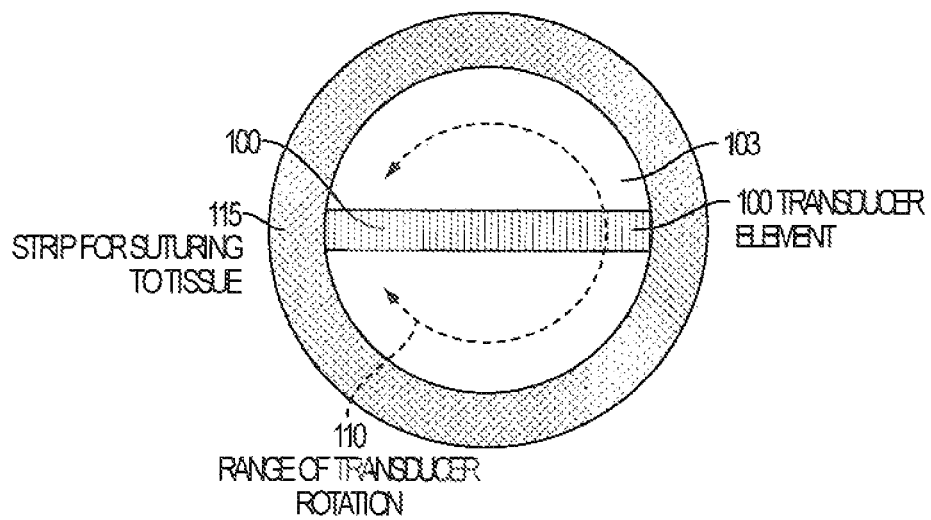
FIG. 1B provides a top surface view of the embodiment of FIG. 1A to be affixed to an internal body wall for ultrasonic imaging.

An arrow 110 of FIG. 1B indicates an angle of rotation of the transducer element 100 or linear array 100 as a rotating diameter at the top of housing 103. In a further alternative embodiment, a single transducer 100 with selectable ultrasound frequency may be mounted as shown in FIG. 3 and driven by linear, X, Y motors to a rectangular position within a disc. A further alternative embodiment substitutes the tine/balloon housing 120 with a second disc housing 103 for bottom imaging/therapy.

Figure 1C:
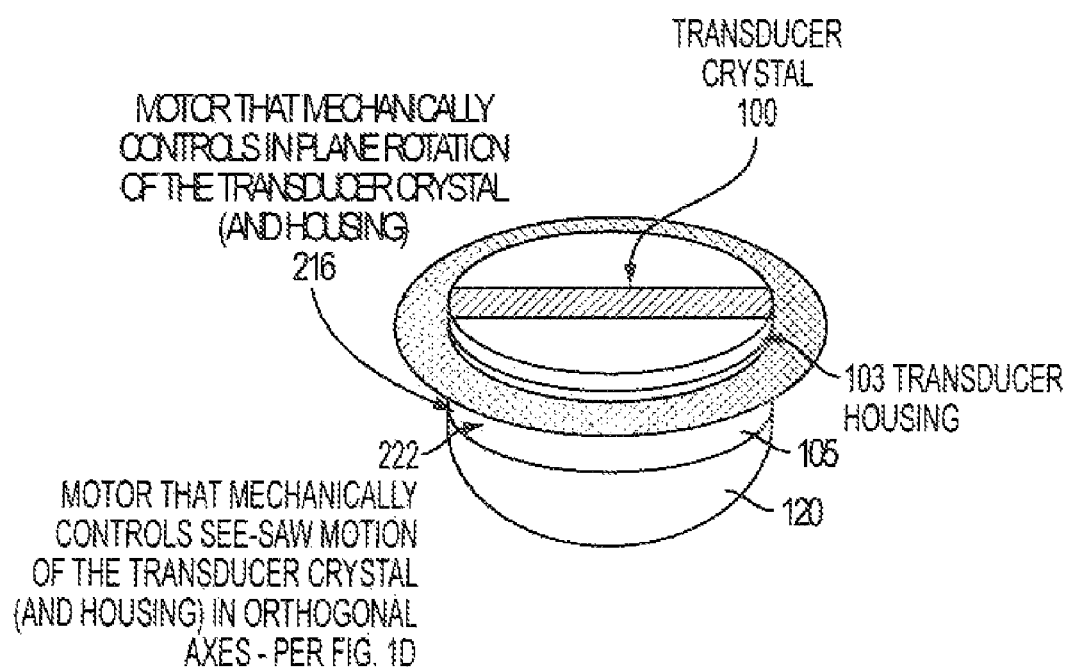
FIG. 1C provides a perspective, functional view of the embodiment of FIG. 1A showing motor housing 105 for rotation motor 216 and twist motor 222 of FIGS. 2 and 3.
Figure 1D:
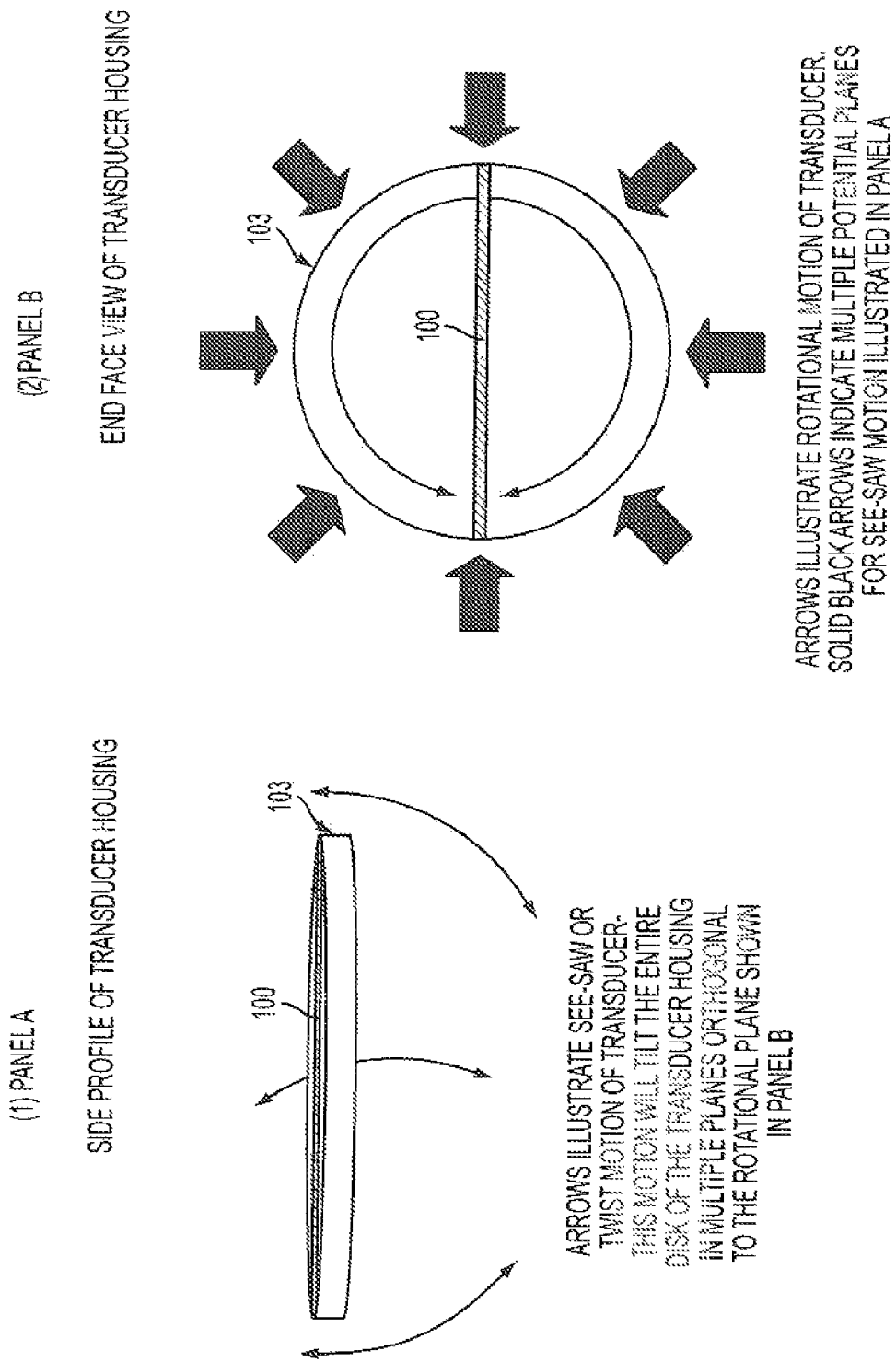
FIG. 1D shows in Panel A (side view—transducer twist) and Panel B (transducer rotation) and so transducer housing twist and rotation details of the implantable device of FIG. 1A.

Typically, referring to FIGS. 1B, 1C and 1D (panel B), an angle of rotation of 360 degrees 110 is provided and, with a curved surface, a full hemispherical, 180° field of twist view (FIG. 1C and FIG. 1D (panel A)) may be obtained, either by selective actuation per FIG. 6 and/or when used with a rotation motor and a twist motor for rotating or twisting linear array 100. Such rotation and twist or selective actuation of sub-elements will permit the collection of a plurality of ultrasonic image planes, for example, of the heart, over which the array 100 of top housing 103 may be located and fixed, for example, to a pericardial or other heart surface by a fixing band 115 or later described screw or extendable tines or inflatable balloons of a housing 120 or motor housing 105. A generally cylindrical top housing 103 as seen from top and side views forms a circular footprint on the organ surface where the motor housing 105 and tine/balloon housing 120 are at the bottom. Motor housing 105, if used as such, also may contain circuitry per FIG. 2 and/or FIG. 6 for actuating the motors and/or selectively actuating transducer 100 sub-elements. The top housing 103 for transducer 100 may be fixed to the surface of a human organ or embedded in tissue underneath bone, for example, in a position at the center of the chest to monitor the heart or in the abdomen to view the gastrointestinal tract, kidney function or prostrate or other function of choice such as brain or joint/muscle function or to provide therapy therefor.

The top surface of the side view (FIG. 1A) shows transducer 100 which may rotate within or on the transducer housing 103. The top surface of housing 103 is intended to be fixed to a patient internal organ or be embedded in internal tissue and may contain an impedance matching substance which may be complimentary to the application of a suitable impedance matching gel. Fastening or securing material 115 is shown in top and side views for fixing the housings 103, 105, 120 to an internal target site with the transducer/impedance matching surface 103 facing the target site to be imaged. The securing material 115 may be a band that may be sutured to an internal organ.

Figure 5B:
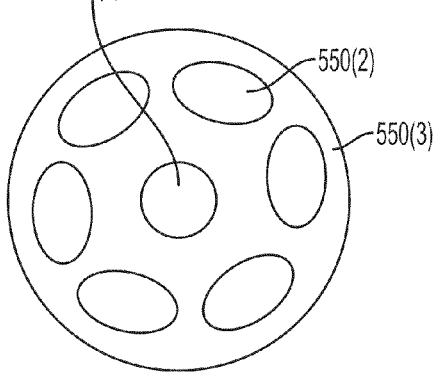
FIG. 5B shows a top down view of the spherical implantable transducer device of FIG. 5A (or the disc of FIG. 1) with an exemplary arrangement of transducers, arrays or sub-elements shown on or just under the surface of the sphere (or disc), for example, in surface apertures.
Figure 5C:
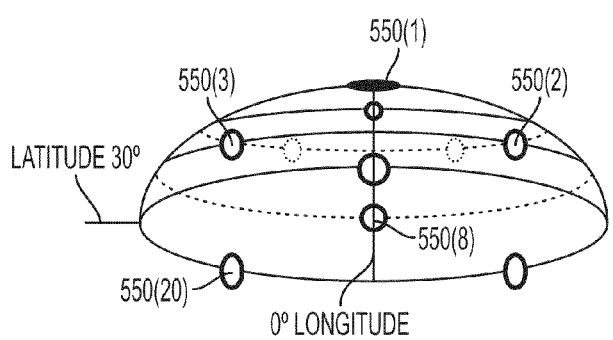
FIG. 5C shows a partial hemisphere of the spherical embodiment of FIG. 5A (or top of disc of FIG. 1) with a further exemplary arrangement of transducers, arrays or sub-elements shown at predetermined latitude and longitude in surface apertures.
Figure 6:
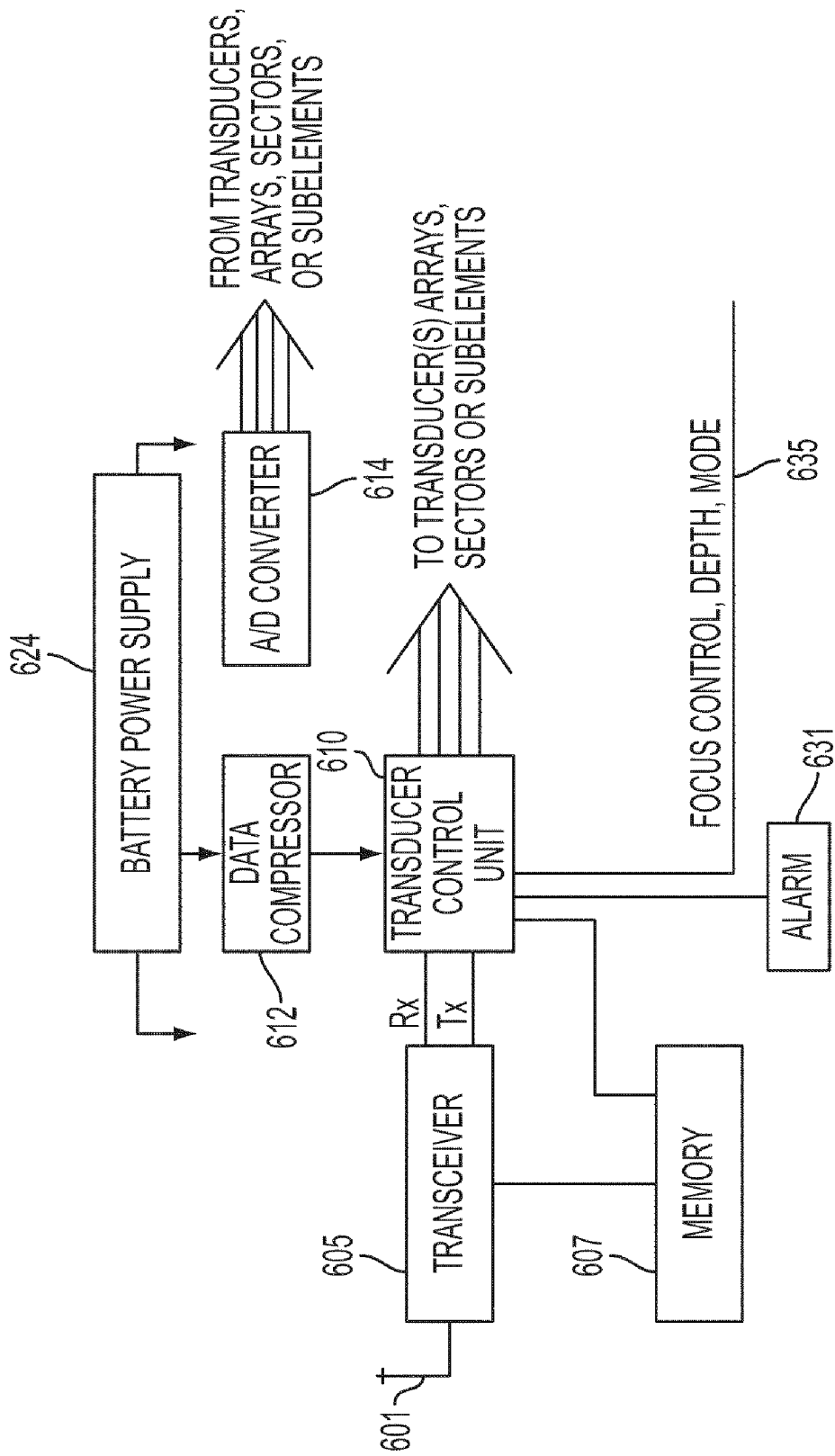
FIG. 6 shows a schematic block diagram for an electronic circuit for switchably selecting a transducer, array, sub-element, or sector of a disc, pellet or spherical implantable transducer device in accordance with one or more aspects according to received control instructions and transmitting image data of the selected transducer array or sub-element via transceiver 601.

Referring to FIG. 1C, within the housing 105 may be also contained at least one motor for rotation 216 and/or one motor for twist or alternatively a circuit (FIG. 6) for selective actuation of a sub-element or sector of sub-elements 550 (FIG. 5B, 5C). Also located within the housing 105, for example, in the vicinity of the one or more motors, if provided, may be a wireless transceiver and antenna (not shown; see, for example, FIG. 2 or 6), a transducer control unit 210, and other circuitry as necessary for receiving and processing motor control or transducer sub-element actuation signals and other known control signals such as on/off, mode, depth, magnification, frequency of operation, power level, focus and the like as will be described with reference to FIG. 4A. If the circuitry has wired rather than wireless transmission and reception, a wire or plurality of control leads as a cable (not shown) may lead from the site of implantation to outside the body in which a disc-shaped housing is implanted. Of course, such wired use may involve at least a semi-permanent body opening that must be kept sterile.

Also, shown in FIG. 2 and contained in housing 105 is a battery or induced power system 224 (FIG. 2) or 624 (FIG. 6) for powering the motors and circuits requiring power. Such a system is not required if a wire is used to power as well as transmit and receive data to/from the implanted device embodiment (disc, sphere, pellet or double disc).

Wireless (or wired) communication may be with a wireless (or wired) work station console (for example, ultrasound imaging unit 1040 (FIG. 10), preferably remote from a patient bedside, which selectively listens for the channel frequency of transceivers 205 (FIG. 2) or 605 (FIG. 6) or to a server communicating with a plurality of work stations and may operate in a similar manner to known private radio or telecommunications wireless channels). It should be noted that one implanted transducer device may output more than one imaging channel at a time, for example, a top image may be provided as well as a bottom image or a side image, depending on actuated transducer sub-elements and there being different directions of ultrasound wave transmission and reception, for example, to provide a stereo image of the same site or different ultrasound images of different target sites.

As will be described herein, motor 216 (FIG. 1C; FIG. 2) may provide rotation (also, rotate the linear arrays 710 of FIGS. 7 and 8) and twist motor 222 may provide twist for linear array 100 of FIG. 1A, 1B, 1C, or array 710 of FIGS. 7, 8 to permit a different direction and field of view of sound wave emission and/or reception.

There may be optionally provided two directions, for example, lengthwise and widthwise (x and y) axis movement in the plane of the human organ surface and according to how a rectangularly-shaped motor arrangement (FIG. 3) is placed in circular motor housing 105 and, further, how the motor housing 105 is placed in the body, i.e. an x and y axis are considered in relation to the housing 105. A single linear motor may comprise an optional screw gear assembly for more accurate linear movement of array 710 or a single transducer (not shown) or sub-element of array 710 lengthwise along the pellet as will be further described herein.

All depicted motors of FIGS. 2 and 3 are preferably micro or miniature motors known in the art for turning, for example, a rotor or screw and may have an optional gear assembly for rotating or twisting the coupled transducer element or linear array 100, 710 at incremental steps such as one degree steps from a vertical or horizontal orientation (vertical shown) through 180 degrees (disc) or 360 degrees (pellet)—clockwise or counterclockwise. In this manner, a linear array 100, 710 may capture 180 or 360 different planes of view at one degree intervals of, for example, a heart or chest cavity under observation, and a three dimensional view may be constructed using known software data analysis processes. Of course, the three dimensional analysis is improved and made stereoscopic if pairs of ultrasound transducers (or more than two arrays) or sub-elements of implantable devices at different observation locations according to FIG. 1 are selectively actuated and used as will be described in conjunction with a discussion of FIG. 6. A transceiver 205, 605 may report the actual rotation position of the linear array 100, 710 to a remote work station or ultrasound remote imaging unit 1040 as a value, for example, between 0 and 180 (disc) or 360 degrees (pellet). The physical location of a wirelessly transmitting implantable device in the human body may be calculated at the work station 1040 by radio frequency triangulation or other means from receiving transmissions from the transceiver 205 and calculating the physical position of a given housing within the human body or determined relative to imaging obtained therefrom.

In an alternative embodiment, the electronic circuit of FIGS. 2, 6 may comprise an input control or selector per FIG. 4A for selecting one of a plurality of locations on the body, such as chest or abdomen, and/or a target organ, such as one of two lungs or the heart, to image by latitude and longitude of a sphere (FIG. 5) or rotation of a transducer 710 of a pellet (FIG. 7) or by other remote control coordinate data.

Typical sizes for a transducer housing 103, 105 as shown in FIG. 1 may be determined according to the diameter of the delivering lumen, for example, less than 20 F (wherein 1 F=0.33 mm). On the other hand, if the implantable transducer of the several embodiments is surgically implanted, the size limitation may not be limited to 20 F but may be, for example, as large as one or two centimeters in diameter and 0.2 to 0.5 centimeters in height, the limitation being the comfort zone of the patient, location of implant and possibly the size of the cavity in which it may be secured, such as the nasal cavity. The height of the cylindrical housing may be similar or less than 20 F if implanted using a catheter/sheath in a minimally invasive manner. The size of a housing 103, 105, 120 of a disc of FIG. 1 (of FIG. 5 (sphere) or of FIGS. 7-9 (pellet)) is directly related to the size of components it contains and should be minimally invasive, cause as little discomfort or dysfunction as possible to the patient and may be deliverable via a catheter or sheath directly to the target site in a body. Certainly, the trend in the electronic arts including mechanical motor arts is toward further miniaturization and integration. Consequently, notwithstanding the given dimensions, it is not inconceivable that a housing 103, 105, 120 and associated components such as transducers and circuits, for example, may be reduced in height or thickness to the range of micrometers or nanometers within the next twenty years. The size of the footprint on a human organ or embedded in human tissue, or whether the device is used internally in a body cavity, may relate to the particular application and not necessarily to the sizes suggested above for housings 103, 105, 120 or for spherical or pellet housings.

Referring briefly to FIG. 3, the surface proximate to an organ or human tissue in which an implantable device having a housing 103, 105, 120 may be embedded may be adapted to receive such a housing within which a rectangular shape and arrangement of linear motors may move micro-rods carrying, for example, a transducer array to a particular x, y coordinate, for example, ranging from 0 to 20 F in one direction to 0 to 20 F in the other direction within its footprint within the body in incremental steps, for example of 0 to 1 F. In a further embodiment as described above, a motor 222 may be provided and mounted to twist a linear array 100 (or array 550 or array 710) as well as provide an incremental angle of rotation, again, within a range of 0 to 180 degrees (or 360° for the pellet) with a default position at 0 degrees, or directly pointing sound waves into the target site, for example, from the north pole 520. In an alternative application, for example, to image a human heart, the x and y motors 218 and 220 may be actuated to improve imaging by moving a location of transducer 225 to another location removed from a partially obstructed ultrasound path or one including undesired reflections, for example, caused by another implanted device or an invasive device used in the vicinity of the heart region of interest.

FIG. 2 provides a schematic block diagram for embodiments and aspects of a wired or wireless implantable device of a motor driven type as shown, for example, in FIG. 1, 5 or 7-9 including a transceiver 205 (which may be a wireless telecommunications transceiver), a transducer control unit 210 which may comprise a microcomputer, a battery 224 including an induction charger, at least one motor 216 for rotating a linear transducer element array, the linear transducer element array 225 and analog to digital circuitry 214 for converting collected image data to digital form for transmission via the transceiver 205, for example, to work station 1040. In FIG. 2, a wireless embodiment of a remotely manipulatable, implantable ultrasound transducer may be assumed and components such as the battery or power supply eliminated in a wired embodiment (because the device may be powered by wire). Battery supply unit 224 (or supply 624 of FIG. 6) is, for example, a rechargeable lithium battery known in the art that powers all units requiring power within a housing 103 (not shown in FIG. 2), a sphere 500 or a pellet implantable device 700.

Transceiver 205 (FIG. 6, 605) wirelessly receives control information and may receive and transmit a digital data signal generally in keeping with FIGS. 4A and 4B via antenna 201 (601). These figures suggest transmission of a serial data stream of image and parameter data; in alternative embodiments, the depicted data of FIG. 4 may be received/sent in parallel format over plural channels (or serial format) or multiplexed on a single channel and in any order including the order shown over wired or by wireless means. Moreover, the depicted data transmitted in each direction may be supplemented by other known control or imaging data and other unit identification data such as server address data. Known telecommunications protocols may be utilized if the transceiver 205, 605 transmits and receives by radio frequency signal such as WiFi, blue tooth, Wimax and the like for a wireless local area network. As is known in the art, infrared and ultrasound may be used as well as other radio frequencies such as in the lower microwave band (for example, less than 2 GHz); (upper microwave frequency transmission would be greatly attenuated through a human body unless the implantable transducer is mounted close to the skin and not too deep within the body). Data according to FIGS. 4A and 4B may be transmitted that is uniquely indicative of a given transmitter, transducer or work station, or the implantable device may transmit on a unique channel, not used by any other transceiver 205, 605.

Alternatively, the data of FIGS. 4A and 4B may additionally comprise a unique server address if a server is host to a plurality of client work stations or secondary back-up work stations. Moreover, the workstation ID of FIG. 4B may be a primary work station, for example, unit 1040 (FIG. 10) and the data signal further comprise an address for one or more secondary work stations. If any other implantable device is wirelessly transmitting and receiving nearby or within the same body, then addressing using a unique address (or telephone number) or other identifier should be used for an implantable device (FIG. 1, 5 or 7-9). Transceiver 205, 605 may receive a data signal from a work station 1040, demodulate the signal and output a demodulated baseband data signal including data per FIG. 4A to transducer controller 210, 610 which may be a microprocessor, application specific integrated circuit or other control circuit which may be designed and fabricated in a manner well known in the art. Radio frequency transmission may also be used in a wired embodiment above DC power (0 frequency) transmitted/received over a lead or wire cable. Transducer controller 210, 610 may run a real time clock and date program synchronized periodically with a real time clock at an associated work station. In the other direction of transmission, the transceiver 205, 605 may receive image data for one or more planes or sequential images and other signal including actual position data (for example, x and y coordinates, magnification, depth, rotation angle, twist angle, longitude and latitude or the equivalent data, time and date and the like) per FIG. 4B from transducer controller 210, 610 for transmission to a uniquely identified remote work station, for example, 1040.

Following the path of a received signal at antenna 205, 605, or from a lead wire or cable, the received signal may be received at radio frequency at transceiver 205, 605 (at RF and converted to baseband), demodulated, if necessary, and a Rx data output control signal passed to controller 210, 610 for processing. Controller 210, 610 authenticates the received signal as directed to it by means of the transmitted unique transducer identification code of FIG. 4A. In addition, the signal may require processing in accordance with well known protocols for decompression, decryption, parity and other data error detection and correction algorithms and the like (not shown). In one embodiment, for example, for multi-planar imaging purposes, a transducer array 100, 225, 710 is linear and may be rotated. A rotate signal which may indicate an angle between 0 and 180 degrees in the case of a disc (360° in the case of a pellet or back to back discs) in incremental steps of, for example, one to five degrees can indicate rotation in a clockwise or counterclockwise direction or indicate an angle to which the transducer array 100, 710 or sub-element is to be rotated (for example, from 90 degrees, actual present position, to 120 degrees, desired position) is received and passed to linear motor 216 having a rotor for rotation using, possibly, an optional gear assembly for turning the linear array 100, 710 to a desired angle of rotation.

In an alternative embodiment, for example, for therapeutic purposes, a direction of sound wave propagation, frequency of transducer operation (preferably selectable and having as large a range as possible), depth (dependent on frequency) and the like signal are received and reported to actuate twist motor 222 to a desired angle of twist of the linear array in addition to a desired angle of rotation via motor 216 to, for example, deliver a therapeutic sound wave to a given body organ or sub-tissue layer at a given transmitted depth, for example, represented by a sound wave power level, within the patient's body from the transducer 100, 225, 550, 710. In an embodiment paired with another implantable unit, the angle of twist and rotation may be synchronized so that one transducer array 100, 550, 710 may cooperate with another transducer array as sound wave transmitter and sound wave receiver for together providing image data either individually or together. Also, a therapeutic transducer (operating at a lower ultrasound frequency range but, if required, for example, for tumors, a high power level) and an imaging transducer (operating within a higher ultrasound frequency range) may be mounted to the same movement system per FIG. 2 or 3 within the same or different disc, sphere, dual disc or pellet housings.

If positioned inside a body cavity such as a nasal, oral, ear or other body cavity and secured there, a disc, pellet, sphere or dual disc housing may contain a transducer which may rotate 360° and be moved by a separate twist motor. The transducer may be moved along the length of, for example, a pellet-shaped housing shaped for the cavity in which it is implanted to different lengthwise positions by a linear motor. The transceiver 205 outputs such transducer control data to controller 210 which then actuates motors 218 for x axis movement and, if needed, motor 220 for y axis movement, 216 for rotation and 222 for twist of transducer element or transducer array 102, 225, 550 and 710 or sub-element thereof as shown, for example, in the arrangement of FIG. 3. Also shown in FIG. 2 are x, y axis 227, 229 which are controlled by motors 218, 220. When arriving at the x, y position of interest, the transducer 100, 225, 550, 710 may be rotated or twisted or rotation and/or twisting/rotation may occur en route to the x, y position of interest. Feedback to the remote work station 1040 may be provided via actual data indicating all parameter values of interest, on/off, focus level, depth, magnification, ultrasound frequency, power level, duration (therapy), x axis, y axis, angle of rotation and angle of twist (most of which are shown in FIGS. 4A and 4B) as well as image data and work station address or identification.

Also, controller 210, 610 may be in receipt of motor control, off/on, focus control, mode, magnification, frequency of operation, power level, depth and other control data which is passed to transducer 102, 225, 550, 710 for proper operation, for example, to regulate the amount of power delivered to transducers for sound wave emission or for focusing the array or for frequency of ultrasound transmission. This control lead or collection of leads is shown as data line 235, 635. If more than one transducer is provided for, for example, simultaneous imaging and therapeutic purposes, then, a selection bit for selecting one or the other transducer or array may be included in the data of FIG. 4A.

The output of transducer array 100, 225, 550, 710 may be raw image (reflected sound wave) data similar to that obtained by a hand-held transducer array known in the art. It may be in analog form and provided to an A/D converter 214, 614 for sampling at an appropriate sampling level, for example, depending on desired image resolution. The data signal output of A/D converter 214, 614 may be further compressed at data compressor 212, 612 prior to formatting at controller 210, 610 for transmission at transceiver 205, 610 and/or storage at memory 207, 607, for example, according to FIG. 4B. These circuits 214, 614 and 212, 612 are shown as separate circuits but may, together with controller 210, 610 be in the form of a single application specific integrated circuit (ASIC) or provided as separate circuits. Memory 207, 607 may be on board a microprocessor chip or provided separately. In one embodiment, memory 207, 607 may comprise a removable memory for uploading, for example, imaging data collected over time to a device for wireless or telecommunications transmission. The image and other data prior to transmission or for long term storage may be temporarily or more permanently stored in memory 207, 607. Similarly, memory 207, 607 may be utilized for temporarily storing control data as received from transceiver 205, 605 and prior to being operated on by controller 210, 610.

Image and associated position data and the like for a given image along with time of day and date may be stored in a fanny pack or personal remote control device worn or otherwise carried by the patient. This assumes a time of day and date clock associated with controller 210, 610 or the time and day may be periodically updated via a transmission to the circuits of FIG. 2 or 6. In, for example, a therapeutic embodiment of an implantable transducer array, the patient wearing or carrying the device may control delivery of therapeutic sound waves via a transducer array 100, 550, 710 and control the direction and depth of transmission. For example, ultrasound has been found to assist in relieving arthritis and other pain, for example, in a hip, shoulder, knee or other joint.

In one embodiment where the circuitry and motors are contained in a housing and implanted in the person, the person may be remotely observed as they go about their daily routine at a remote work station 1040. For example, an implanted ultrasound transducer array located so as to monitor a major organ may detect a change that requires medical attention. For example, the heart rate measured for an observed heart organ may trigger an alarm 231. In such an instance, alarm 231 may trigger a vibrator on the patient's body or may signal a remote work station 1040 to signal the wearer to report to a facility. The alarm 231 may also indicate a point in time when a memory 207 is full of un-transmitted images, and the wearer must upload their memory image data of memory 207, 607 or report to a work station 1040 or other telecommunications or radio receiver facility for image data upload.

In a further embodiment according to FIG. 2, there may be provided a wired remote control for use by a wearer to control application of therapeutic ultrasound energy and so control primarily rotation and twist motors and control ultrasonic frequency range to deliver therapeutic treatment, for example, in the event that a workstation operator is out of wireless contact with the wearer or the wearer has been pre-instructed as to a particular therapeutic treatment that may correct a given complication. The priority of control of an implantable ultrasound assembly according to FIGS. 1 (disc), 5 (sphere) and 7-9 (pellet) is surgeon or attending physician, workstation operator and patient. Ultrasound waves are for the most part harmless. On the other hand, a user may be provided only limited control over, for example, frequency and intensity or power level while a surgeon/physician will have unlimited control especially in emergency intervention situations.

FIG. 3 provides an overview of a mechanical arrangement to be contained within a housing 100 of a disc, sphere 500 or pellet (FIGS. 7-9) embodiments of an implanted transducer unit for manipulating an associated transducer or linear transducer array in two directions, for example, along an x axis and a y axis and to provide an angle of rotation and a twist angle at a desired x, y coordinate pair to redirect a sound wave emitted by a transducer or linear array of transducer elements whereby it is envisioned that a footprint on an internal patient body surface may be approximately rectangular or square. Assume the rectangular assembly of FIG. 3 comprises guide wires or rods 300, 301, 302 and 303 on which are provided y-axis rod 304 which may be moved in an up and down direction shown via a corresponding motor 220 and gear assembly not shown to incremental steps along the y axis. Similarly, there may be provided x-axis rod 305 which may be moved to the left or the right direction shown via corresponding motor 218 and a gear assembly not shown. X-axis rod 305 and Y-axis rod may intersect at a desired point where an array or element may be affixed via further rotation motor 216 and twist motor 222 within a disc, sphere or pellet (motors 716, 722). For example, rotor 306 of motor 216 (in combination with an optional gear assembly 109) may provide rotation of a mounted transducer array 100, 225, 550 or 700 or transducer sub-element thereof to a predetermined or desired angle of rotation. Motor 222 may provide twist 307 to a linear array or sub-element 100, 225, 550, 710 to change direction of sound wave transmission or reception with 90 degrees—straight down—being a default position for twist.

FIG. 4A provides an exemplary signal content format for providing motor control of an implanted transducer or transducer array 100, 550, 710 of FIGS. 1, 5 and/or 7-9 in a direction from a work station 1040 to an implanted wireless transducer including a unique transducer transceiver identifier if wireless transmission is utilized. The format also provides for known control such as on/off, focus, depth, mode and the like. An exemplary control word (not shown) that may be used in addition to a single bit on/off command is a two bit word that may describe an application of the implantable device at a given "on" time where the four positions may comprise clot dissolution, heat therapy, cancer tumor therapy and imaging. According to various embodiments, motor control data may comprise an x direction or a longitudinal axis direction, a perpendicular or y direction, an angle of rotation, an angle for twist of a transducer or array as depicted. There is also a DRR field that may be used for all other control mentioned herein including but not limited to: magnification, depth, frequency range, power level, focus, resolution, transducer select data for a plurality of transducers, arrays or sub-elements, an indicator of a controlling work station 1040 or user (patient) or other control indicator that may be included in this field. Other control or other data to be transmitted in a direction from work station 1040 or other user towards an identified implanted transducer assembly may come to mind of one of ordinary skill in the art of ultrasound apparatus. Motor control data may be transmitted, for example, in the form of ultimate desired position or as an incremental step from an actual position or other way that may come to mind of one of skill in the art.

FIG. 4B provides an exemplary signal content format for providing a reply signal from an implanted transducer or transducer array of FIG. 1 (disc), 5 (sphere) or 7-9 (pellet) in a direction from an implanted wireless or wired transducer including a unique work station identifier of, for example, work station 1040, if wireless transmission is utilized. The wireless transmission may be directed via a server and a server identification provided (not shown) serving one of a plurality of workstations identified by workstation identifier. The format provides for feedback of actual location data of the position of the transducer or transducer array within or the selected imaging sector in, for example, latitude and longitude coordinates per FIGS. 5 and 6. The actual location data may comprise an x axis or longitudinal axis dimension, a perpendicular y axis dimension, an angle of rotation, an angle of twist, a latitude and longitude as well as image data and physical location within the human body, such as a code for the pericardium. There may be an indicator as to the transducer or transducer array associated with the image data and a time and date indicator provided by the real time clock program of the transducer control unit 210, 610 for the time and date of collection of the image.

In an embodiment including a therapeutic transducer or a combination therapeutic/imaging transducer, the frequency of operation and the power level or magnitude of transmission and a measure of the reflected wave may be signaled as well as an image of the region of interest, for example, a location of a blood clot or tumor. The actual location data of the implanted transducer may be compared to a desired location, for example, of the blood clot/tumor to determine if the remotely controlled implanted transducer or transducer array has reached a desired position so that imaging and/or therapeutic dilution of the blood clot/tumor may begin with focus control being especially important, for example, via a plurality of focused sub-elements of the implanted transducer. The implanted transducer of the several embodiments may separately treat the blood clot/tumor at a first frequency range and power level and be actuated to image the volume in which the blood clot/tumor is located to determine its degree of dissolution.

Moreover, the imaging and control data may be collectively utilized by a work station 1040 to determine the location of the implanted transducer assembly, for example, underneath the skin surface or within a body cavity. As shown in FIGS. 1 and 2, in one embodiment, the device 100 is in the form of a disc and may comprise a second disc mounted underneath a top side to form a pill shape having a top side (for example, facing an organ) and a bottom side facing outward of the organ for practically full spherical ultrasound imaging.

A housing can be fabricated of any conventional materials used in forming catheters, sheaths, and interventional devices. Preferably any such material will be generally non-bioreactive so that the device will not stimulate, for example, tissue reactions that may result in generation of scar tissue which will make recovery of the device more challenging, for example, requiring surgical removal. For example, when in the form of an implantable transducer as a disc, sphere or pellet or dual disc, the exterior housing may be fabricated of, for example, silicone, Teflon, polyurethane, PVC, or elastomeric hydrogel, for example, AQUAVENE®. Preferably, a non-bioreactive jacket or cover may permit smooth removal, for example, by pulling a cord (which may contain a communication wire) if the implanted device, for example, is used for post-surgery monitoring for a relatively short period and so limit the chance of infection at the retrieval site. Preferably, any connecting cable, wire or retrieval cord, if required or used, will exit a single skin opening which will be maintained sterile, for example, in a manner similar to that used for heart assist devices where pumps are located outside a body.

The implantable transducer 100, 550, 710 incorporates an imaging system that provides a user with visualization within the body during a procedure. The imaging system is particularly useful in minimally invasive procedures wherein direct visualization of the target site is unavailable. In one embodiment, the imaging system can be in the form of an ultrasound system. Ultrasound systems are well-known and, thus, although described and shown herein with reference to one embodiment, the general features and components of the ultrasound systems may be varied in accordance with conventional systems.

Transducers 100, 550, 710 can be in accordance with conventional transducers. For example, in some embodiments, the transducers comprise piezoelectric materials such as PZT ceramics. The transducers may also be of any size, with such size being limited by discomfort and cavity size, the physical miniaturization limits of the size of the disc, sphere or pellet to, for example, a size, if implanted by a catheter/sheath to the diameter of the catheter/sheath or to less than 20 F. As transducer size is decreased, the quality of the image provided may also decrease. On the other hand, ultrasound transducers are becoming smaller and smaller over time. The smallest sized transducer that provides adequate imaging may be generally used so as to minimize the required size required of the implanted transducer. For example, presently, 2-3 mm×2 mm transducers will generally require a housing of 5-6 F. In certain embodiments, the transducers or a sub-element thereof may have dimensions of less than 1 mm.

The transducers of implantable devices as described herein can generally be mounted on the surface or just under the surface of a disc, double disc, sphere or pellet embodiment by providing one or more mounting apertures (not shown) in which the transducers can be fit and held. Various adhesives may be used, as necessary, to hold transducers in place in respective disc, sphere or pellet housings.

Referring now to FIG. 5A, there is shown a perspective view of a spherical implantable transducer device in accordance with aspects herein where 0° latitude represents a ring analogous to the equator of the earth and 90° latitude represents the north or south pole. While this embodiment may comprise motors for rotation and twist of an associated transducer (for example, a linear array arranged around half the equator 510), the spherical embodiment is more conducive to exclude the use of motors and utilize a switchable selection of one or more transducers, arrays or sub-elements for actuation according to latitude and longitude and an associated field of view and resolution. In FIG. 1A, there is shown, by way of example, an equator 510 at 0° latitude while 0° longitude is represented by a vertical line in FIG. 5C.

An embodiment per FIG. 5 of an implantable transducer may be in the shape of a sphere and, similarly to a "globe" of the earth, individual transducers may be placed at latitudinal and longitudinal intersections about the "globe." Such an embodiment has the advantage of not requiring any motors to move a transducer. It has an advantage of "instant" imaging because there would be a time delay to move a motor. Per FIG. 5B, a plurality of transducers 550 are seen spaced about a hemisphere in an exemplary embodiment where transducer 550(1) is located at the north pole 520 or south pole 530. By way of example, the transducer or array or plurality of sub-elements thereof at 550(1) may direct a beam directly out from the page with a selectable frequency, power level, field of view, depth and range while transducers 550(2) and (3) and other depicted transducers may direct a beam at an other than orthogonal direction (unless under the influence of a twist motor). Transducers 550(2) and 550(3) or sub-elements thereof at different locations may receive transmissions from each other from themselves or from transducer 550(1) or a sub-element thereof to provide three-dimensional and stereo imaging or provide more intensive therapies at a focal point of a plurality of ultrasound transmissions from plural sub-elements, for example, to bolster delivered power level and/or direct emitted ultrasound waves, for example, at different portions of a blood clot, tumor.

The "globe" of an embodiment of FIG. 5 may comprise a material that is transparent to ultrasound transmission, reception. The transducers may be then placed just under the material or in apertures of the material of the sphere facing outward. Individual transducers may be selectively actuated by remote control to capture an image in the direction in which a selected transducer faces according to the circuit of FIG. 6 and/or moved according to portions of the circuit of FIG. 2. For example, a transducer 550 may be located at 20 degree increments about the "globe" "equator" 510 (18 transducers 550). There may be a central-to-the-sphere electronic circuit (FIG. 2, 6) which will receive and selectively move and/or actuate the transducers 550 or combinations of sub-elements thereof to obtain different views of different target sites surrounding the globe or sphere or provide different therapies. A limitation on such an embodiment is the number of individual transducers required to populate the "globe."

More transducers are required at the "equator," for example, 18 at, for example, 10 degrees latitude points, 30 degrees and 60 degrees, and only one required at the north pole 520 and south pole 530. One design might thus have 1, 6, 10, 14, 18, 18, 14, 10, 6 and 1 transducers at 20 degree increments about 180 degrees of latitude and dispersed in longitude as well. (This totals 98 transducers). A reasonable number of transducers then to populate the globe may be between thirty and one hundred and fifty depending on the field of view desired for each transducer. Preferably, each of these may be a sub-element and separately actuated. For binary addressing, 32 or 64 or 128 may be a more reasonable number of sub-elements populating the globe for individually addressing in 5, 6 or 7 bits of data as per, for example, FIGS. 5B and 5C. The "globe" will be implanted in surrounding tissue via various means for stabilizing the globe within the patient which may comprise screws, retractable tines or dual inflatable, sandwiching balloons; (see FIG. 9, for examples of securing means). The tines can also be moved simultaneously by a central motor or manipulating shaft tool 910 to an extended position or the screw(s) turned, the tines extended or the sandwiching balloons inflated by an implanting catheter or sheath (not shown). After the "globe" embodiment (FIG. 5) is placed and secured in the patient at a desired target location, the tines extended or the screw turned or sandwiching balloons inflated to secure the "globe," the implanting imaging catheter or sheath or manipulatable shaft tool 910 is withdrawn.

Figure 7:
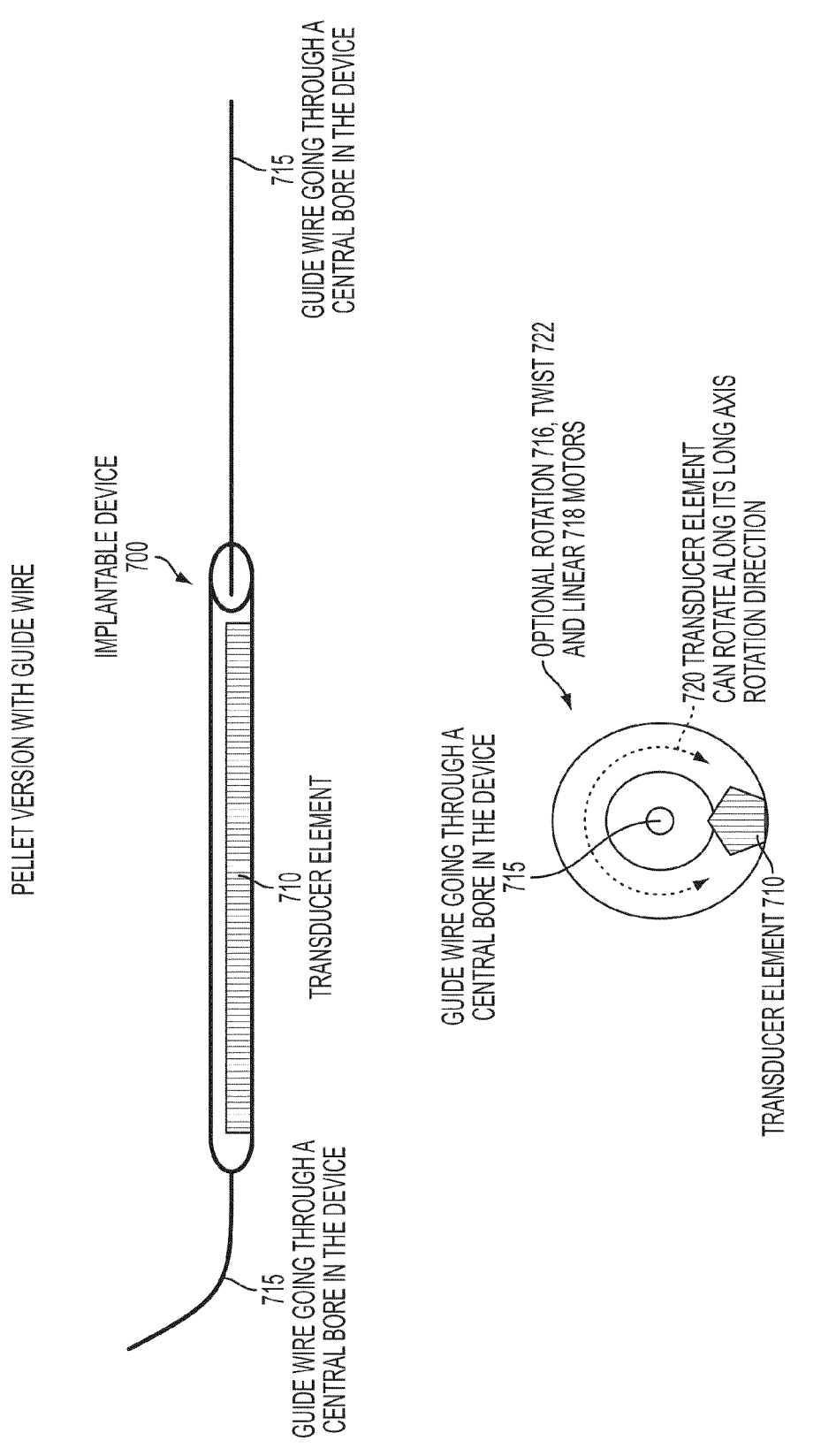
FIG. 7 shows a side and cross-sectional views of an implantable pellet version including a guide wire running along its length and having at least a rotational motor per FIG. 2 for rotating a linear transducer running the length of the pellet about the circumference of the pellet.

A further alternative embodiment comprises a "globe" in which a single transducer or transducer array may rotate around the globe along a perimeter (such as the equator or a meridian longitude in a similar manner to the transducer 710 rotating about the longitudinal axis of a pellet as shown in FIG. 7 but in 360° of directions (except where vision or therapy may be impeded where bone, gas, tines or screws or centrally located motor(s), stabilizers/circuits may obstruct viewing/therapy). The single transducer (or array) will be pointed via a motor/circuits, the motors/circuits secured to the edges of the globe and located centrally at the core of the sphere. The motor/circuits are attached to one or more transducers 550 or sub-elements thereof so that the transducer may capture an image from practically any direction (latitude and longitude coordinate) of the globe.

Transducers 550 are seen in top down view in FIG. 5B of the spherical implantable transducer device of FIG. 5A (or the disc of FIG. 1) with an exemplary arrangement of transducers 550, arrays or sub-elements shown on or just under the surface of the sphere (or disc) comprising transducers 550(1), (2) and (3) among others depicted but not numbered. These can be selectively actuated by an electronic circuit housed in the sphere of FIG. 5 as per FIG. 6.

FIG. 5C shows a partial hemisphere of the spherical embodiment of FIG. 5A (or top of disc of FIG. 1) with a further exemplary arrangement of transducers, arrays or sub-elements shown at predetermined latitude and longitude. Transducer 550(1) is located at the north pole 520 and/or south pole 530. Transducer 550(20) is shown located at 30° latitude and just to the left of the meridian at 0° longitude. Transducer 550(8) is shown mounted at 0° longitude, just up from 30° up from the equator 510. Transducers 550(2) and 550(3) are shown located just down from the north pole 520 at different longitudes.

Referring now to FIG. 6, there is shown a schematic functional block diagram of an electronic circuit. When used for imaging, transducer control unit 610 selects a transducer, array, sector of a sphere or combination of sub-elements by means of individual control leads to them. These are further controlled by a lead 635 for focus control, depth, mode and so on. The transducers report their output by individual leads to A/D converter 614 for compression at data compressor 612 and transmission by transceiver 605 via transducer controller 610. Memory 607 may be used for temporary storage of data and alarm 631 may be used as described above with respect to the motor embodiment of FIG. 2. In some applications, both selective actuation per FIG. 6 and motor actuation per FIG. 2 are combined to selectively actuate or move transducers and provide them with control data.

Figure 8A:
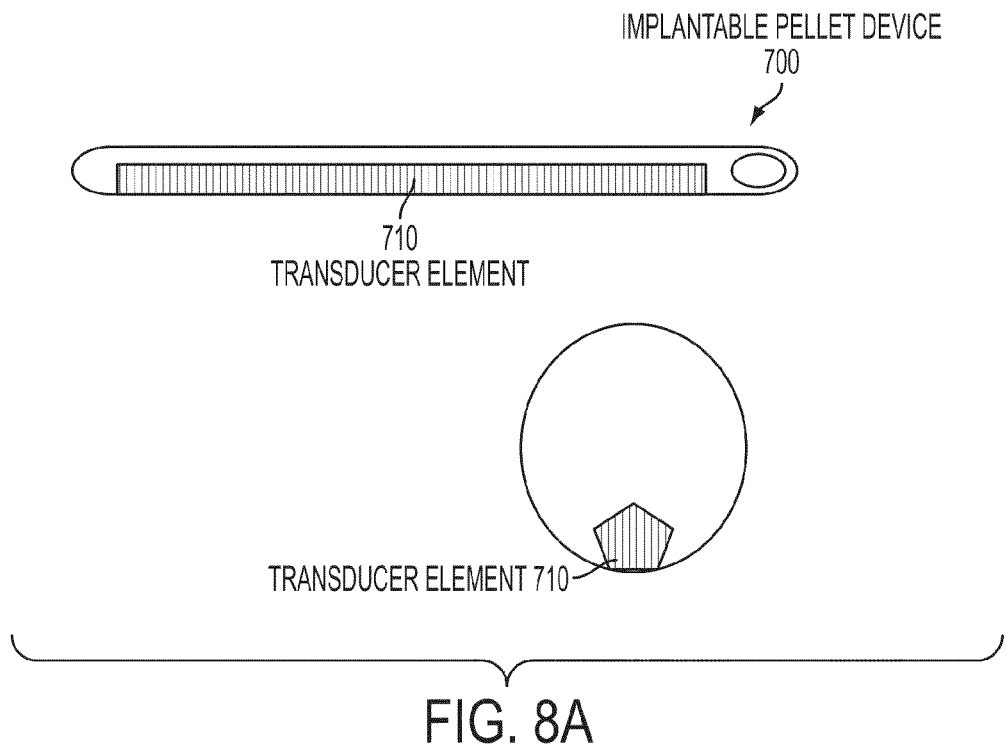
FIG. 8A shows side and cross-sectional views of a pellet embodiment similar to that shown in FIG. 7 but constructed of solid material (no guide wire) where a transducer array may be similarly rotated about the pellet's circumference.
Figure 8B:
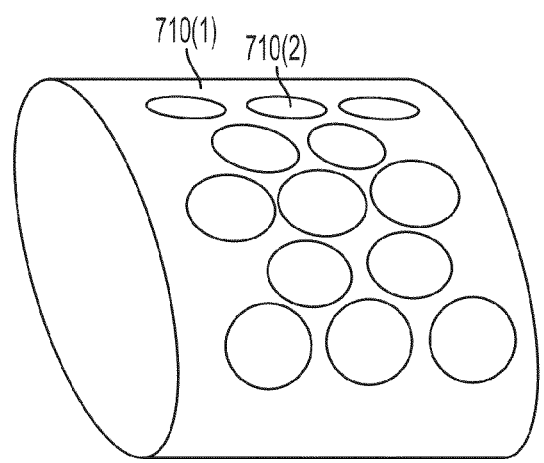
FIG. 8B shows an enlarged cross-section of a pellet having transducer elements spread along its length and around its periphery for selective actuation, for example, in dispersed surface apertures and selected for actuation according to a circuit of FIG. 6.
Figure 9:
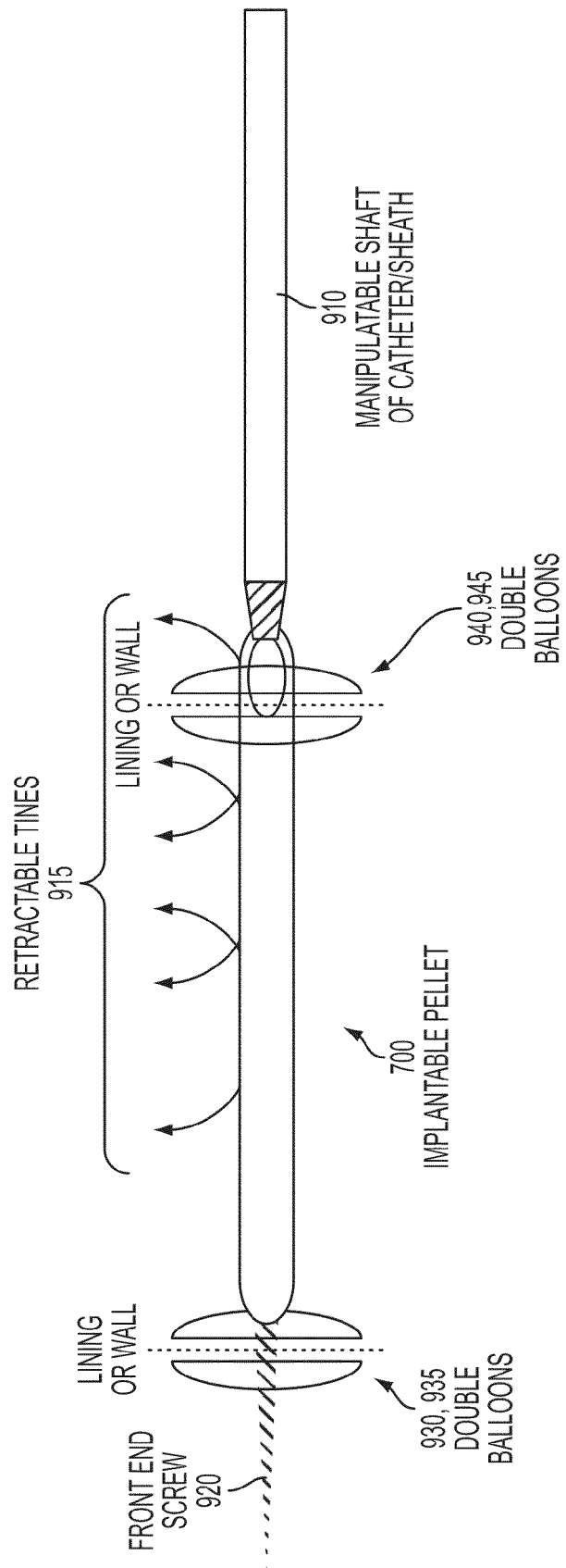
FIG. 9 provides details for delivering and securing a pellet (disc or sphere) whereby a manipulatable shaft may be moved through a delivery lumen to deliver the pellet to the organ for securing, for example, by a front end screw, actuable tines (which may be extended for securing and retracted for removal) or double balloons or a combination thereof.

Referring now to FIGS. 7-9, a pellet embodiment of an implantable device for ultrasound imaging/therapy will be discussed. FIG. 7 shows a side view (top) and a cross-sectional view (bottom) of an implantable pellet version 700 including a guide wire 715 running along its length through a central bore or lumen. The guide wire is used for locating the implantable pellet 700 and is removed after the pellet is located and secured in place, for example, with reference to FIG. 9. For example, an introducer needle of a catheter/sheath can be inserted into a target area. The guide wire 715 is then threaded into the target area. The implantable pellet device 700 is then advanced over the guide wire 715 to the target site. The device 700 is released by a delivery device and its securing mechanisms per FIG. 9 activated. The guide wire 715 is then removed. In a wired (not wireless) version, a connecting cable may exit from an entry site of a body's skin surface and connected to a work station 1040 where images may be interpreted by a technician or connected to another remotely controlled device for joint communication with a work station 1040.

Implantable pellet device 700 may comprise, in one embodiment, at least a rotational motor 716 for rotating a linear transducer 710, array, plurality of sub-elements thereof running the length of the pellet 700 about the circumference of the pellet 700. A direction of rotation 720 of transducer 710 is shown around the pellet 700 through a full range of 360°. Once a lengthwise transducer 710 reaches a rotational angle between 0° and 360°, the transducer 710 may be twisted in its place using a twist motor 722 to obtain different fields of view. Moreover, if transducer element 710 is in a singular form or smaller form, a linear motor 718 may, for example, turn a lengthwise screw gear (not shown) or in an alternative known manner move a transducer 710 along the length of pellet 700.

Rotation 716, twist 722 and linear 718 motors are optional. The transducer 710 may be constructed of sub-elements and so may be similarly constructed as the design of sphere 500 to comprise a plurality of transducers and individually actuable sub-elements thereof that may be selectively actuated along the length and about the circumference of the pellet 700 by a selective actuation electronic circuit per FIG. 6.

FIG. 8A shows side and cross-sectional views of a pellet embodiment similar to that shown in FIG. 7 but constructed of solid material (no guide wire) where a transducer array may be similarly rotated about the pellet's circumference. Referring to FIG. 8A, a solid pellet version 700 is shown having a transducer element 710 running along its length. Such a device may preferably be equipped with at least a twist motor 722 to twist the transducer 710 in place so as to image/provide therapy to a volume or body organ at which transducer 710 may be pointed. Similarly, to the version of FIG. 7, the pellet 700 of FIG. 8 may be rotated by a rotation motor 716, or comprise selectively actuable transducer 710 sub-elements and the solid pellet 700 secured in place as shown in FIG. 9.

Referring now to FIG. 8B, a pellet embodiment 700 is shown in enlarged cross-section have a plurality of transducer elements 710(1) and 710(2) or sub-elements spaced about its length and periphery and so selectably actuated via a circuit similar to that of FIG. 6. Both the embodiments of FIGS. 7 and 8 may be sized appropriately for the application and delivery means.

FIG. 9 provides details for delivering and securing a pellet of FIG. 7 or 8 (disc or sphere) whereby a manipulatable shaft 910 may be moved through a delivery lumen of an associated catheter/sheath or used by itself during surgery to deliver the pellet 700 to an organ or other target site for securing, for example, by a front end screw 920 or actuable tines 915 (which may be extended for securing and retracted for removal by manipulation of controls at a proximate end of manipulatable shaft 910) or pairs of sandwiching balloons at a distal end, 930, 935 of the pellet 700 or at a proximal end, 940,945 of the pellet 700. For example, manipulatable shaft 910 may comprise temporary holding means for delivery at a distal end and a releasing means at its proximal end for releasing the placed pellet 700. Moreover, manipulatable shaft 910 may be connected via the distal ends to tines extension means and a turn of a knob of the proximal end may extend the tines and a reverse turn retract the tines. Manipulatable shaft 910 may comprise first and second lumen (not shown) lengthwise for inflating first a distal balloon, 930 or 935 and then a proximal balloon 935, 945 for sandwiching a body wall or lining (shown in dashed lines) at the distal end or proximal end of implantable pellet 700. Screw 920, wherever placed on a disc, pellet, double disc or sphere, may be of bioabsorbable material or be permanent and non-bioreactive. Sutures and a jacket or strip may be likewise constructed and used. So the screw, sutures and jacket may be absorbed into the patient and removed if temporary placement is preferred, for example, for pellet 700 by a cord or wire (not shown).

A process and structure of inflatable, sandwiching balloons are described in U.S. patent application Ser. No. 11/871,219, filed Oct. 12, 2007, incorporated herein by reference in its entirety and published as US 2008/0183080. Once a body wall or lining is pierced, for example, by a distal tip (for example, screw 920) of an implantable device as seen in FIG. 9 or by an introducer needle of a catheter/sheath, a distal sandwiching balloon 930, 940 located in a corresponding associated circumferential distal or proximal indentation (not shown) is first inflated once the distal sandwiching balloon has passed by an internal body wall or lining to be sandwiched. Distal balloon 930 is inflated if the implantable device is to be located on the proximal side of the internal body wall or lining or, the implantable device may be turned around, and distal balloon 940 in a proximate circumferential indentation (not shown) is inflated if the implantable device is to be located on the internal side of a sandwichable internal wall or lining. The distal balloon 930 or 940 is inflated via inflation/deflation lumen (not shown) running the length of manipulatable tool 910 and at least a portion of a delivery sheath/catheter. The inflation/deflation lumen also extend to the locations of each depicted pair of sandwiching balloons (only one pair being needed). The first inflated distal balloon 930, 940 is pulled to the internal lining or wall. Then, the corresponding proximal balloon 935 or 945 is inflated to complete the sandwiching of the internal wall or lining. The combination of the distal and proximal balloon pair when inflated secure the implantable pellet 700 (disc, double disc, sphere or other embodiment) at the puncture site at the sandwiched internal wall or lining. In one application, for example, the internal lining or wall is punctured, the pellet embodiment advanced to a point where a distal balloon is within the wall or lining, the distal balloon is inflated and drawn back toward the wall or lining and a proximal balloon of an appropriate balloon pair inflated sandwiching the wall or lining (shown in dashed lines) at the point of puncture. Each balloon pair operates similarly. If a balloon pair is mounted on one or the other end of the pellet (or other implantable device), the device need not be equipped with two pairs of balloons. The implantable device may be rotated appropriately depending on whether the implantable device will be inside or outside the sandwiched wall and may be delivered by either end.

In some embodiments, one or more Micro-Electro-Mechanical Systems (MEMS) can be mounted in or on an implantable transducer device 100, 500 or 700 for use both internal to the device, for example, as motors of FIG. 2 or for extension or retraction of tines, for example per FIG. 9 or external uses. MEMS systems may include, for example, mechanical elements (beams, cantilevers, diaphragms, valves, plates, and switches), sensors, actuators, and electronics. MEMS also can be provided to function as tiny sensors and actuators. For example, MEMS can be incorporated in an implantable device for measuring and monitoring blood pressure or pressures in other organs proximate to the implantable transducer.

In some embodiments, the implantable device 100, 500 or 700 can further be integrated with other non-ultrasound imaging modalities including infrared, laser, optical coherence, fiber optic instruments including, but not limited to endoscopic mapping. A wire or cable to the device may incorporate an optical fiber.

The present device 100, 500, 700 also can be used to provide a three-dimensional mapping system solely using the incorporated ultrasound system in connection with other imaging modalities such as ultrasound, computed tomography, infra-red, OCT, magnetic resonance, videoscopy which may be external to the body.

Figure 10:
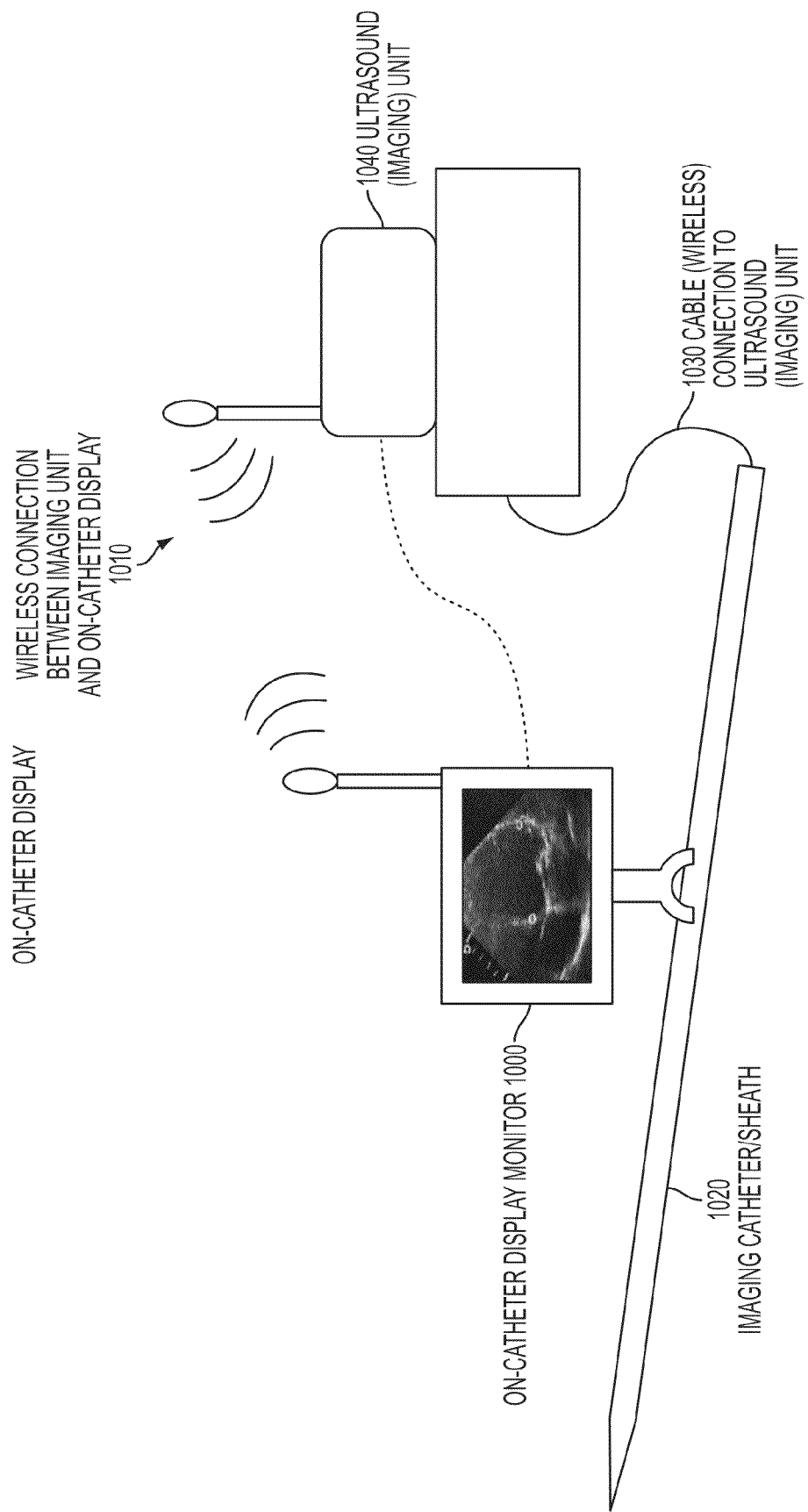
FIG. 10 provides details of mounting a small display on an imaging catheter or sheath at a proximal end; the display may receive signals from an external ultrasound imaging unit (work station), from an implantable device per FIG. 1, 5 or 7-9, from a catheter/sheath front-facing transducer or from a surface mounted transducer by switching wired or wireless imaging channels.

Referring now to FIG. 10 an on-catheter (or sheath) display 1000 is shown which may be used with any of the catheter or sheath devices 1020 described and suggested by U.S. patent application Ser. No. 12/285,779 filed Oct. 14, 2008 of the same inventor and recently published as US 2009/0105597 on Apr. 23, 2009. On-catheter or sheath display 1000 is intended to be mounted at a proximal end of an imaging catheter or sheath 1020 for providing, for example, a surgeon or other user with direct imaging from within the body operated upon. The display 1000 may be covered with a custom sterile drape (not shown) such that the screen and any connecting cable are sterile and do not interfere with the operating field. The display 1000 may be affixed to the catheter or sheath 1020 by any means known in the art preferably including a ball-socket joint so that the surgeon's viewing angle may be adjusted during use. Although not shown, there may be more than one such display attached to a catheter or sheath in alternative embodiments to the depicted embodiment. Moreover, the screen of display 1000 may be divided in half for two channels or into fourths for four viewing channels and the selection circuitry so designed as to allow a user to select more than one channel for viewing at the same time by the surgeon or user. Moreover, the display 1000 may be provided with interactive remote control input controls for selecting one of therapeutic and imaging function, direction of viewing and the like. The display 1000 may be an LED or other miniature display known in the art, for example, of wireless telephony or miniature digital cameras. Consequently, the display screen size may be less than three by four inches.

The display 1000 may incorporate circuitry, not shown, for changing predetermined wireless channels, selecting more than one channel or transmitting control information for communicating, for example, with work station 1040 and/or with an implanted transducer via work station 1040 or directly according to the several embodiments disclosed herein or with a surface-mounted or other external ultrasound imaging device (not shown). Further interactive remote controls (not shown) may be provided for selecting, for example, therapy or imaging, direction of imaging, depth, contrast, resolution, focus, mode, gain and the like for each sub-element of each device in a sterile manner without having to use work station 1040 but rather work through its communication capabilities or directly with the various therapeutic and imaging devices used in the operating suite.

Access of an implantable device to other organs, structures, and spaces not specifically discussed herein can be performed in similar fashion with appropriate procedural modifications specific for the particular organs, structures or spaces. All United States patent application and patent documents mentioned herein are incorporated by reference herein in their entirety. Further, while several preferred embodiments have been described using specific terms, such description is for illustrative purposes only, and it is to be understood that changes and variations may be made without departing from the spirit or scope of the following claims.

I claim:

1. A remotely controllable, implantable imaging/therapeutic transducer device capable of being embedded within a living body, the device comprising
a first housing part for a transducer array;
a second housing part for a rotation motor and a twist motor;
the transducer array, extending along one of a diameter and a length of the first housing part for the transducer array, the transducer array being located in the first housing part, the transducer array comprising a plurality of selectable sub-elements for selective actuation and the transducer array being capable of rotation and twist as the first housing part rotates and the transducer array twists with respect to the second housing part for rotation and twist motors;

a transducer controller for controlling the transducer array and the rotation and twist motors to one of rotate and twist the transducer array respectively, the transducer controller for selecting a sub-element of the transducer array for actuation and for selecting an ultrasound frequency of operation of the selected sub-element of the transducer array for one of therapy and imaging when in use;

a transceiver of the device for communicating with said transducer array in a transmit and a receive direction, the transceiver adapted for wirelessly receiving remote control data from a source external to the living body when in use and for receiving image data via said transducer controller from said selected sub-element of the transducer array when selected for imaging, the transceiver adapted for wirelessly transmitting the received image data to a destination external to the implantable imaging/therapeutic device during use; and an anchoring portion structurally connected to the device and adapted for anchoring the implantable/therapeutic device in a proper position within a living body during use.

2. The device as recited in claim 1, said device comprising a disc shape and being of a non-bioreactive material, a circular top of said disc-shaped device comprising the first housing part for the transducer array, the transducer array extending along a diameter of the first housing part and adapted to be rotated by a rotation motor and twisted by a twisting motor of the second motor housing part of the device through an angle of rotation and an angle of twist determined by said received remote control data.

3. The device as recited in claim 1, said device comprising a pellet shape and being of a non-bioreactive material, the transducer array being disposed linearly along a length-wise direction of the pellet-shaped device and the transducer array being adapted to be rotated by a rotation motor circumferentially about a circular cross-section of the pellet-shaped housing to obtain a 360° range of imaging/therapy about the pellet-shaped device when in use.

4. The device as recited in claim 3, further comprising a twisting motor for twisting the transducer array through an angle of twist determined by said received remote control data.

5. The device as recited in claim 1, said device comprising a pellet shape and being of a non-bioreactive material, the transducer array being disposed linearly along a length-wise direction of the pellet-shaped housing and comprising a plurality of sub-elements, the transducer array being adapted to be rotated by a rotation motor circumferentially about a circular cross-section of the pellet shaped device to obtain a 360° range of imaging/therapy about the housing responsive to receipt of said remote control data when said transceiver is in use, the sub-elements of the transducer array being selectively actuable by said transducer controller responsive to said received remote control data when said transceiver is in use.

6. The device as recited in claim 1, wherein said device comprises a disc shape and said anchoring portion comprises a suturing strip structurally connected to the second motor housing part of the disc shaped device.

7. The device as recited in claim 1 wherein said device comprises a pellet shape and said anchoring portion comprises a pair of inflatable, sandwiching balloons.

8. The device as recited in claim 1, said device comprising a disc shape and being of a non-bioreactive material, the transducer array being in a circular top surface of the disc along a diameter of the top surface and adapted to be rotated by a rotation motor of the second motor housing part through an angle of rotation determined by said received remote control data, the second motor housing part being structurally connected to the anchoring portion, the anchoring portion comprising a suturing strip surrounding the second motor housing portion.

9. A remotely controllable, implantable imaging/therapeutic transducer device capable of being anchored within a living body and adapted to be implanted in soft tissue when in use, said device comprising a substantially spherical shape, said device having a plurality of apertures dispersed about its surface, each aperture for receiving a transducer array comprising a plurality of selectively actuable sub-elements, the plurality of apertures each for receiving one transducer array, said apertures for selectively actuated transducer arrays of selectively actuated sub-elements being located at one and at an opposite pole and substantially equally dispersed about a central circumference of the substantially spherical shaped device, the transducer arrays being located within the apertures of the substantially spherical shaped device, the transducer array of each aperture being mounted to provide a smooth surface of said substantially spherical-shaped device, each transducer sub-element of each transducer array being adapted to be individually controlled by wirelessly received remote control data and to be selectively actuated by a transducer sub-element controller as to actuation frequency and each transducer array of each aperture being selectively actuable, the device comprising an anchoring means adapted to anchor the device within the living body and a wireless transceiver adapted for communicating imaging data from a selectively actuable transducer array to a wireless transceiver external to the living body and for wirelessly receiving said remote control data when in use.

10. The device as recited in claim 1, said device comprising a disc shape, said device further comprising an analog to digital converter connected to the transducer array for converting analog imaging data to digital imaging data and a data compressor for compressing said digital imaging data.

11. The device as recited in claim 1, said device comprising a disc shape, said device further comprising a memory connected to said transducer controller and to said transceiver for temporary storage of data.

12. The device as recited in claim 11, further comprising an alarm circuit, the memory storing normal parameter data for a human body and the alarm circuit capable of being triggered via said transducer control unit when received parameter data for a human body in which the device is implanted during use is outside a range of normal parameter data.

13. The device as recited in claim 1, said device comprising a disc shape wherein said anchoring portion comprises bioabsorbant material and comprises a suturing strip attached to the second motor housing part.

* * * * *